(12) United States Patent
Pizzato et al.

(10) Patent No.: US 9,198,811 B2
(45) Date of Patent: Dec. 1, 2015

(54) MODULAR INSTRUMENT TRAY

(71) Applicant: Medtronic Xomed, Inc., Jacksonville, FL (US)

(72) Inventors: Michael Pizzato, San Francisco, CA (US); Jerry Burttram, Maryville, TN (US)

(73) Assignee: Medtronic Xomed, Inc., Jacksonville, FL (US)

( * ) Notice: Subject to any disclaimer, the term of this patent is extended or adjusted under 35 U.S.C. 154(b) by 0 days.

(21) Appl. No.: 14/019,649

(22) Filed: Sep. 6, 2013

(65) Prior Publication Data

US 2014/0069841 A1    Mar. 13, 2014

Related U.S. Application Data

(60) Provisional application No. 61/698,271, filed on Sep. 7, 2012.

(51) Int. Cl.
*A61F 17/00*    (2006.01)
*A61B 19/02*    (2006.01)
(Continued)

(52) U.S. Cl.
CPC .............. *A61F 17/00* (2013.01); *A61B 19/026* (2013.01); *A61B 19/0256* (2013.01); *A61B 19/0271* (2013.01); *B25H 3/026* (2013.01); *B25H 3/06* (2013.01); *A61B 2019/0213* (2013.01); *A61B 2019/0225* (2013.01);
(Continued)

(58) Field of Classification Search
CPC ...... B65D 25/10; B65D 25/107; A61F 17/00; A61L 2/26; A61B 19/0271

USPC ......... 206/570, 370, 363, 499, 501, 503, 505, 206/514; 422/300; 220/23.88, 23.83
See application file for complete search history.

(56) References Cited

U.S. PATENT DOCUMENTS 4,024,590 A * 5/1977 Wendt .............................. 4/628
4,053,280 A * 10/1977 Salisbury ..................... 206/363
(Continued)

FOREIGN PATENT DOCUMENTS

GB            00794         9/1914
JP      2002102252 A        4/2002

OTHER PUBLICATIONS

International Search Report and Written Opinion mailed Jan. 15, 2014 for PCT/US2013/058441, claiming benefit of U.S. Appl. No. 14/019,649, filed Sep. 6, 2013, which claims benefit to U.S. Appl. No. 61/698,271, filed Sep. 7, 2012.

(Continued)

*Primary Examiner* — Steven A. Reynolds
(74) *Attorney, Agent, or Firm* — Harness, Dickey

(57) ABSTRACT

A modular instrument kit configured to receive a plurality of instrument trays therein. At least one of the trays includes a planar base, a rear wall orientated at an angle relative to the base, a flange, and an instrument support configured to support a plurality of surgical instruments. The at least one tray is configured to be seated on a generally planar surface in a free-standing position to support the plurality of surgical instruments such that tips of the instruments extend upward so as to be readily viewable in an operating room. The at least one tray is configured to be hung from a generally vertical surface with the rear wall generally flush against a first surface of the generally vertical surface and the flange in contact with a second surface of the generally vertical surface that is opposite to the first surface.

23 Claims, 21 Drawing Sheets

(51) Int. Cl.
*B25H 3/02* (2006.01)
*B25H 3/06* (2006.01)

(52) U.S. Cl.
CPC  *A61B 2019/0258* (2013.01); *A61B 2019/0272* (2013.01); *A61B 2019/0277* (2013.01); *A61B 2019/0278* (2013.01); *A61B 2019/0279* (2013.01); *A61B 2019/0281* (2013.01)

(56) References Cited

U.S. PATENT DOCUMENTS

| | | | | |
|---|---|---|---|---|
| 4,094,431 | A * | 6/1978 | Wheeler | 220/23.4 |
| 4,717,024 | A * | 1/1988 | Djezovic | 206/581 |
| 4,730,725 | A * | 3/1988 | Marshall et al. | 206/63.3 |
| 4,798,292 | A * | 1/1989 | Hauze | 206/439 |
| 5,092,480 | A * | 3/1992 | Waterston | 220/23.4 |
| 5,174,453 | A * | 12/1992 | Stoeffler | 206/570 |
| 5,339,955 | A * | 8/1994 | Horan et al. | 206/370 |
| 5,779,053 | A * | 7/1998 | Partika et al. | 206/570 |
| 5,913,422 | A * | 6/1999 | Cote et al. | 206/370 |
| 6,048,503 | A * | 4/2000 | Riley et al. | 422/298 |
| 6,193,932 | B1 * | 2/2001 | Wu et al. | 422/28 |
| 6,230,888 | B1 | 5/2001 | Frieze et al. | |
| 6,783,004 | B1 * | 8/2004 | Rinner | 206/368 |
| 7,748,529 | B2 * | 7/2010 | Foreman et al. | 206/370 |
| 7,980,517 | B2 * | 7/2011 | Zoland et al. | 248/37.6 |
| 8,272,508 | B2 * | 9/2012 | Bettenhausen et al. | 206/370 |
| 8,453,977 | B2 * | 6/2013 | Zoland et al. | 248/37.6 |
| 2002/0191938 | A1 | 12/2002 | Sheetz et al. | |
| 2006/0213794 | A1 * | 9/2006 | Foreman et al. | 206/370 |
| 2010/0270442 | A1 | 10/2010 | Zoland et al. | |
| 2013/0105346 | A1 * | 5/2013 | Ramkhelawan et al. | 206/370 |

OTHER PUBLICATIONS

International Preliminary Report on Patentability and Written Opinion mailed Mar. 19, 2015 for PCT/US2013/058441, claiming benefit of U.S. Appl. No. 14/019,649, filed Sep. 6, 2013, which claims benefit to U.S. Appl. No. 61/698,271, filed Sep. 7, 2012.

* cited by examiner

MODULAR INSTRUMENT TRAY

CROSS-REFERENCE TO RELATED APPLICATIONS

This application claims benefit of U.S. Provisional Patent Application No. 61/698,271 filed on Sep. 7, 2012. The entire disclosure of the above application is incorporated herein by reference.

FIELD

The present disclosure relates to a modular instrument kit, such as for surgical instruments.

BACKGROUND

This section provides background information related to the present disclosure which is not necessarily prior art.

Surgical instruments, such as forceps, scissors, trocars, picks, sponges, elevators, speculas, mallets, suction tubes, and various other instruments, particularly instruments for ear, nose, and throat (ENT) procedures, are often organized and stored in sterilized trays or containers. While the containers sometimes include a variety of instrument mounts, the containers often lack sufficient mounts and features that allow the instruments to be sufficiently organized in an order that will maximize storage efficiency and access during surgical procedures. For example, ENT instruments are often merely seated within the storage container on a bottom surface thereof in an unorganized fashion. Therefore, a container with enhanced surgical instrument mounts, particularly for ENT instruments, sufficient to arrange and present the instruments for use during surgery in a more efficient and accessible manner would be desirable.

SUMMARY

This section provides a general summary of the disclosure, and is not a comprehensive disclosure of its full scope or all of its features.

The present teachings provide for a modular instrument kit including a container configured to receive a plurality of instrument trays therein. At least one tray includes a planar base configured to support the at least one tray upright on a planar surface. A flange is configured to hang the tray from a sidewall of the container. An instrument support is configured to support a plurality of surgical instruments and couple the plurality of surgical instruments to the at least one tray.

The present teachings further provide for a modular instrument kit configured to receive a plurality of instrument trays therein. At least one of the trays includes a planar base, a rear wall orientated at an angle relative to the base, a flange, and an instrument support configured to support a plurality of surgical instruments. The at least one tray is configured to be seated on a generally planar surface in a free-standing position to support the plurality of surgical instruments such that tips or handles of the instruments extend upward so as to be readily viewable in an operating room. The at least one tray is configured to be hung from a sidewall of a container of the kit, or on any other surface in an operating room such as an operating room table, with the rear wall generally flush against a first surface of the sidewall and the flange in contact with a second surface of the sidewall that is generally opposite to the first surface.

The preset teachings also provide for a modular instrument kit including a container, a first tray, and a second tray. The first tray is configured to be seated within the container and includes a plurality of instrument mounts. The second tray includes a planar base configured to support the second tray upright on a planar surface, a flange configured to hang the second tray from a sidewall of the container, and an instrument support configured to support a plurality of surgical instruments and couple the plurality of surgical instruments to the second tray.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

Example embodiments will now be described more fully with reference to the accompanying drawings.

Figure 1:
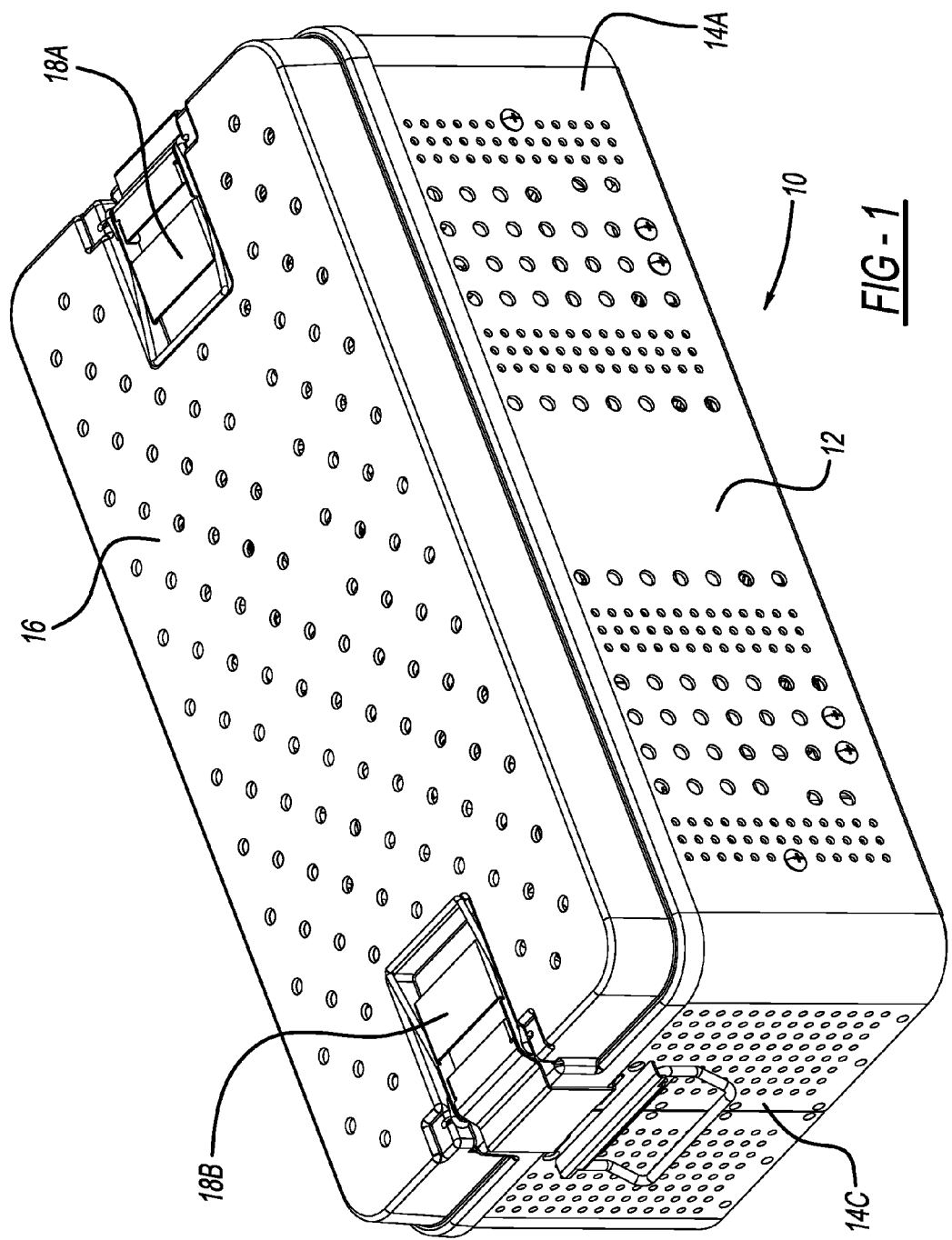
FIG. 1 is a perspective view of a modular instrument kit according to the present teachings.
Figure 2:
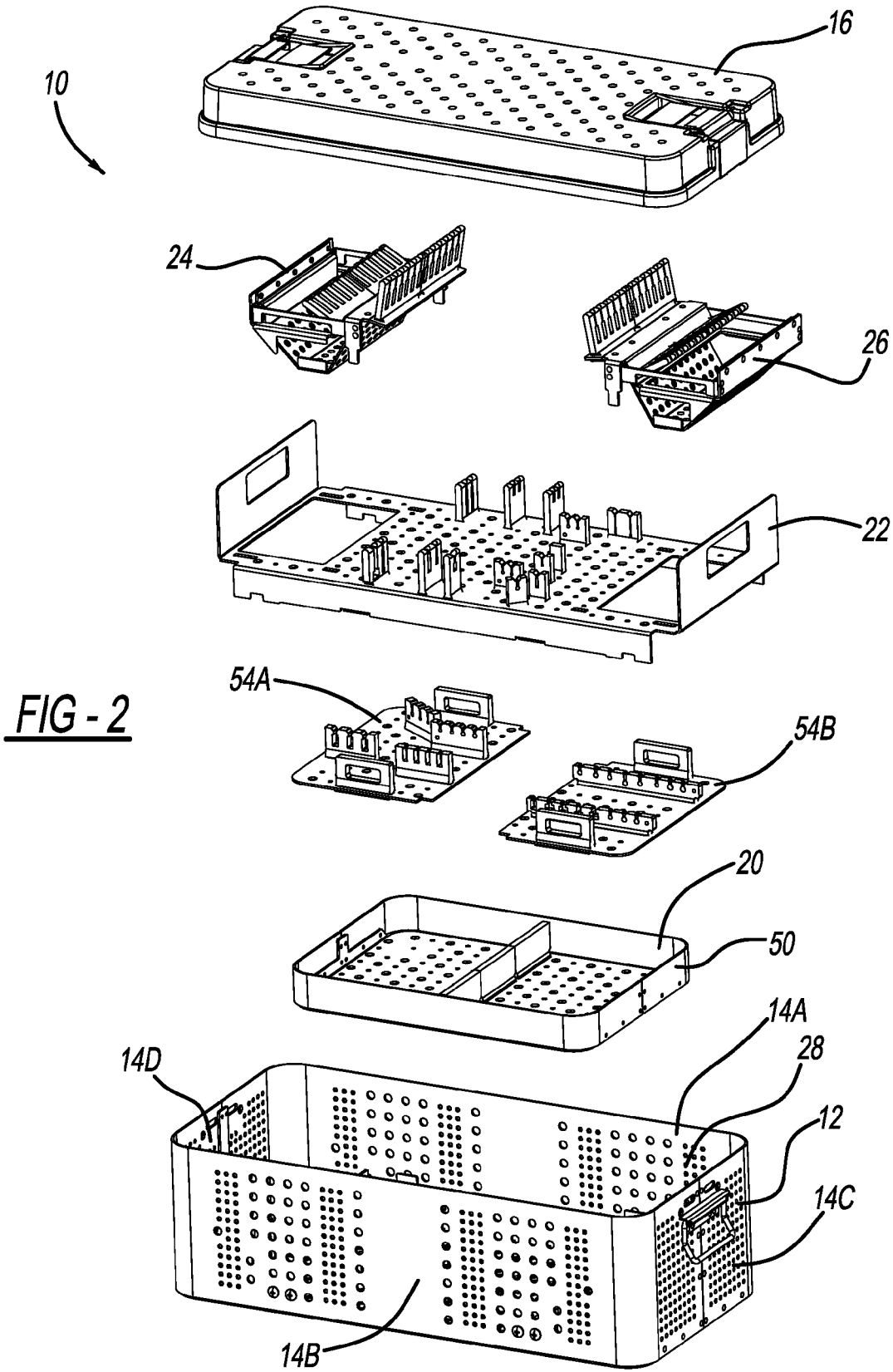
FIG. 2 is an exploded view of the modular instrument kit of FIG. 1.
Figure 3:
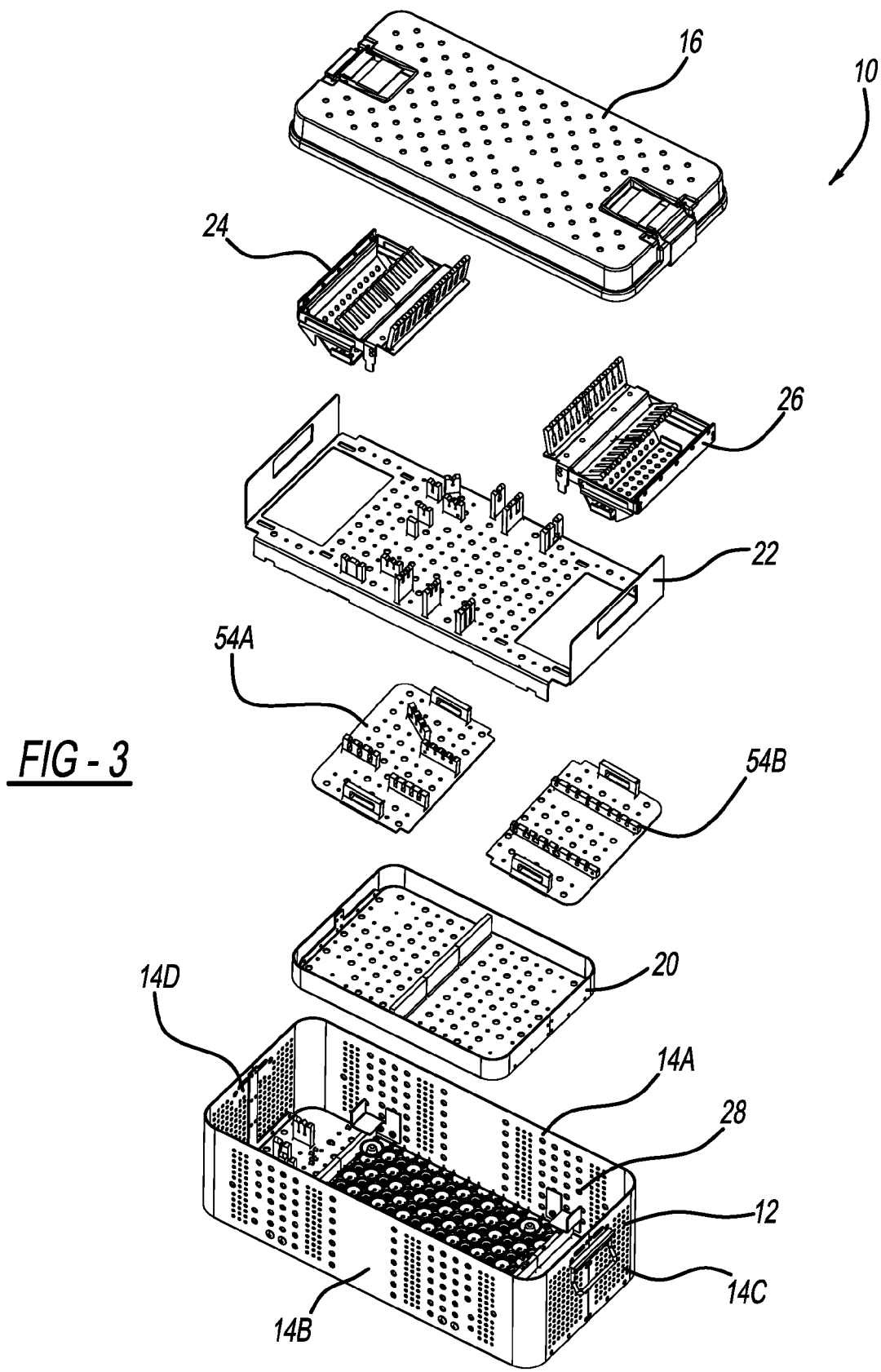
FIG. 3 is another exploded view of the modular instrument kit of FIG. 1.

With initial reference to FIGS. 1-3, a modular instrument kit according to the present teachings is generally illustrated at reference numeral 10. The modular instrument kit 10 includes a container 12 with four sidewalls 14A-14D and a lid 16 removably mounted to the container 12. The lid 16 includes a first lock 18A and a second lock 18B. The first and second locks 18A and 18B are configured to couple with the container 12 to selectively secure the lid 16 to the container 12. The first and second locks 18A and 18B can be any locking device or feature suitable to secure the lid 16 to the container 12.

The container 12 can be made of any suitable material sufficient for the storage of medical instruments therein and for use in an operating room. For example, the container 12 can be made of a suitable material that can be sterilized in an autoclave, such as aluminum. The lid 16 can be made of any suitable material also sufficient to be sterilized in an autoclave, for example, such as a suitable polymer.

Figure 4:
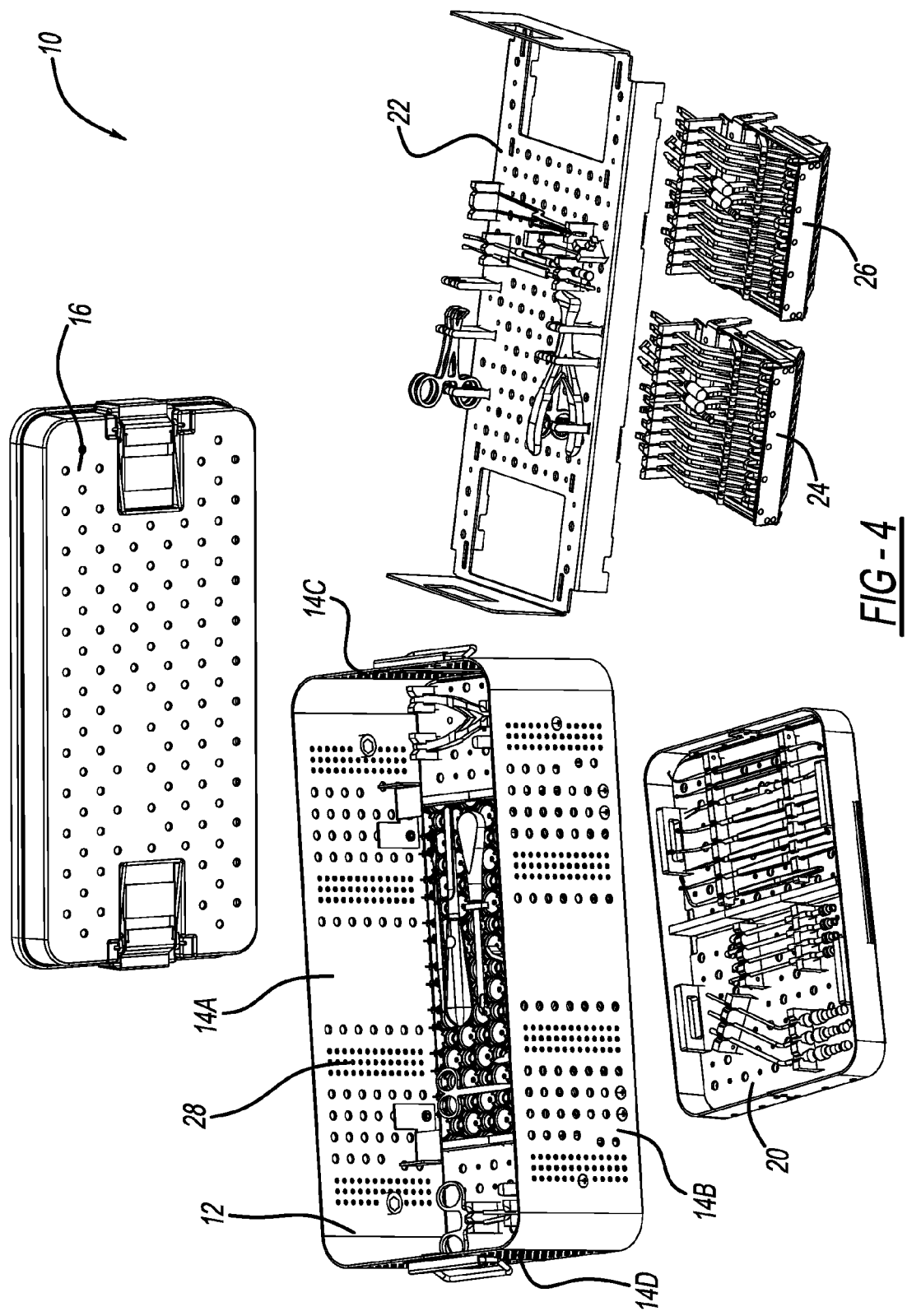
FIG. 4 illustrates various instrument trays and racks of the modular instrument kit.

With continued reference to FIGS. 1-3 and additional reference to FIG. 4, the modular instrument kit 10 further includes a first tray 20, a second tray 22, a first instrument rack 24, and a second instrument rack 26. Each of the first tray 20, the second tray 22, the first instrument rack 24, and the second instrument rack 26, can be removably seated and housed within a storage chamber 28 defined by the sidewalls 14A-14D of the container 12. The container 12, the first tray 20, the second tray 22, the first rack 24, and the second rack 26, will now each be individually described in further detail.

Figure 5:
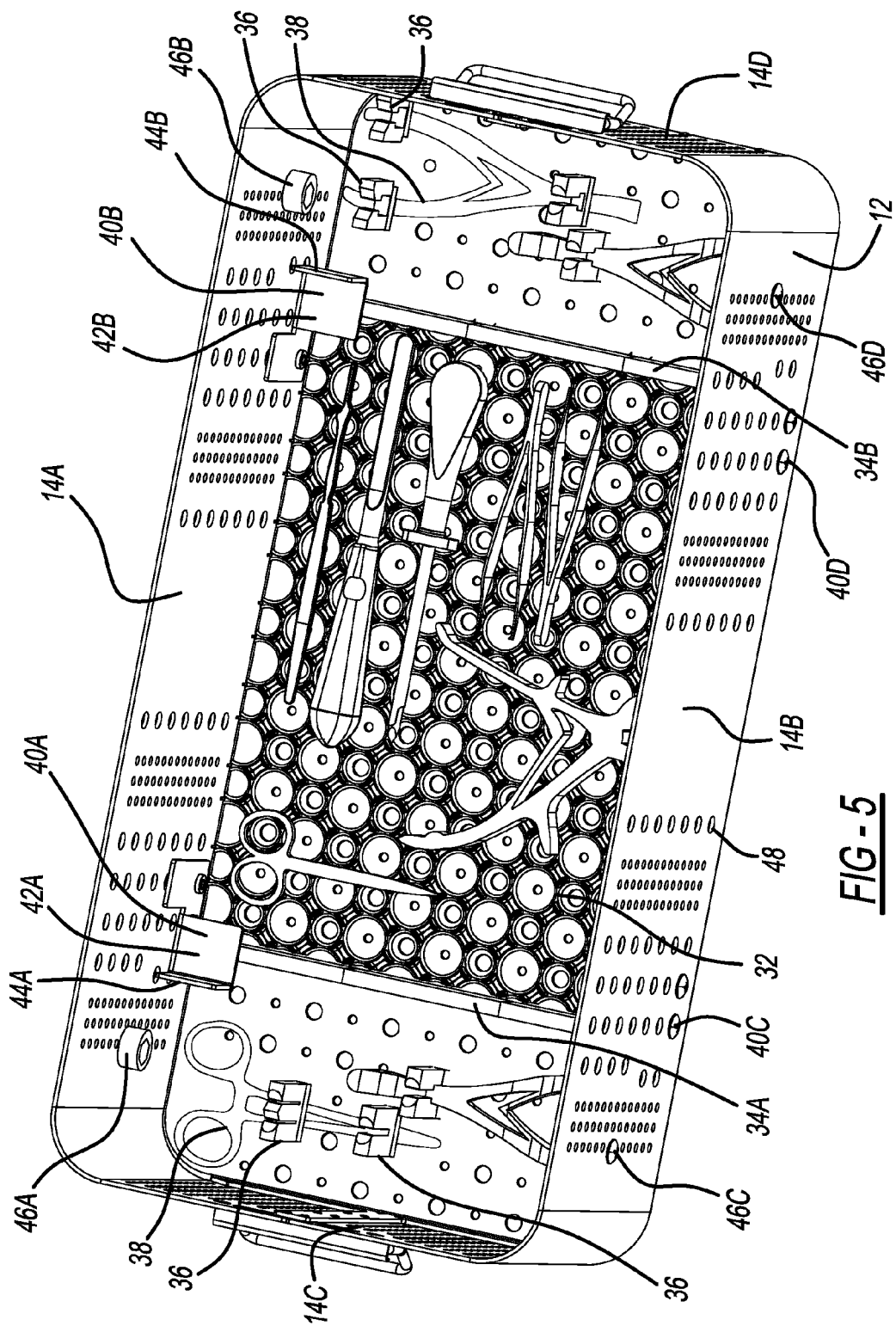
FIG. 5 is a perspective view of a container of the modular instrument kit.

With additional reference to FIG. 5, the container 12 includes a base 30, which is generally planar. The sidewalls 14A-14D extend from the base 30 to define the storage chamber 28. The first and second sidewalls 14A and 14B are spaced apart from one another on opposite sides of the base 30 and generally extend parallel to one another. The second and third sidewalls 14C and 14D extend generally parallel to one another and perpendicular to the first and second sidewalls 14A and 14B. The third and fourth sidewalls 14C and 14D are at opposite ends of each of the first and second sidewalls 14A and 14B. The sidewalls 14A-14D can be modular portions fastened together in any suitable manner, or may be unitary, as illustrated in FIG. 5 for example.

Seated on and fastened to the base 30 is an instrument storage pad 32. The instrument storage pad 32 is generally planar and made of any suitable material to retain instruments thereon, such as silicone. The instrument storage pad 32 may have raised sidewalls 34A and 34B at opposite ends thereof to help retain instruments on the storage pad 32. The instrument storage pad 32 is particularly suitable for retaining larger instruments thereon, such as trocars, suture carriers, and forceps. The instrument storage pad 32 can be mounted to the base 30 in any suitable manner to prevent the storage pad 32 from becoming disconnected from the base 30. For example, the base 30 can include any suitable retention feature or adhesive sufficient to mate with the instrument storage pad 32 to retain the instrument storage pad 32 against the base 30.

The base 30 may further include a plurality of base instrument retention members 36 on opposite sides of the instrument storage pad 32. The base instrument retention members 36 are generally sufficient to clamp or secure a portion of a surgical instrument thereto to prevent the instruments from moving within the storage chamber 28, particularly during transportation of the modular instrument kit 10. To facilitate placement of instruments at the base 30 and in connection with the base instrument retention members 36, the base 30 can include instrument outlines 38 drawn thereon or etched within the base 30. The instrument outlines 38 can be an outline of any instrument suitable to be mounted at the base 30.

With continued reference to FIG. 5, the first sidewall 14A includes a first retention flange 40A and a second retention flange 40B. The second sidewall 14B includes a third retention flange 40C opposite to the first retention flange 40A and a fourth retention flange 40D opposite to the second retention flange 40B (only fasteners of the third and fourth retention flanges 40C and 40D are viable; the third and fourth retention flanges 40C and 40D are substantially similar to the first and second retention flanges 40A and 40B respectively).

With respect to the first retention flange 40A, it generally includes a first portion 42A which extends from the first sidewall 14A generally parallel to the base 30, and a second portion 44A that extends from the first portion 42A. The second portion 44A extends generally perpendicular to the first portion 42A, and thus the second portion 44A is also generally perpendicular to the base 30. The second portion 44A extends from a side of the first portion 42A that is generally opposite to the second retention flange 40B. The second retention flange 40B is substantially similar to the first retention flange 40A. The second portion 44B of the second retention flange 40B extends from a side of the second retention flange 40B that is opposite to the first retention flange 40A. The third retention flange 40C, which extends from the second sidewall 14B in a position generally opposite to the first retention flange 40A, is configured and arranged substantially similar to the first retention flange 40A. The fourth retention flange 40D, which extends from the second sidewall 14B opposite to the second retention flange 40B is arranged generally similar to the second retention flange 40B. The first, second, third, and fourth retention flanges 40A-40D are spaced apart from the base 30 to support the first tray 20 within the storage chamber 28 spaced apart from and suspended above the base 30, as further described herein.

Extending from the first sidewall 14A between the first retention flange 40A and the third sidewall 14C is a first retention pin 46A. Extending also from the first sidewall 14A, but between the second retention flange 40B and the fourth sidewall 14D, is a second retention pin 46B. Extending from the second sidewall 14B opposite to the first retention pin 46A is a third retention pin 46C. Extending from the second sidewall 14B opposite to the second retention pin 46B is a fourth retention pin 46D. Each of the first, second, third, and fourth retention pins 46A-46D extend to within the storage chamber 28 to support the second tray 22 within the storage chamber 28 spaced apart from both the base 30 and the first tray 20, as further described herein. The sidewalls 14A-14D can further include a plurality of openings 48 defined therein that extend therethrough to provide the storage chamber 28 with suitable ventilation. As illustrated throughout the figures, the container 12, the first tray 20, the second tray 22, the first rack 24, the second rack 26, and the lid 16 all include similar openings to facilitate autoclaving of the modular instrument kit 10 to sterilize it.

Figure 6:
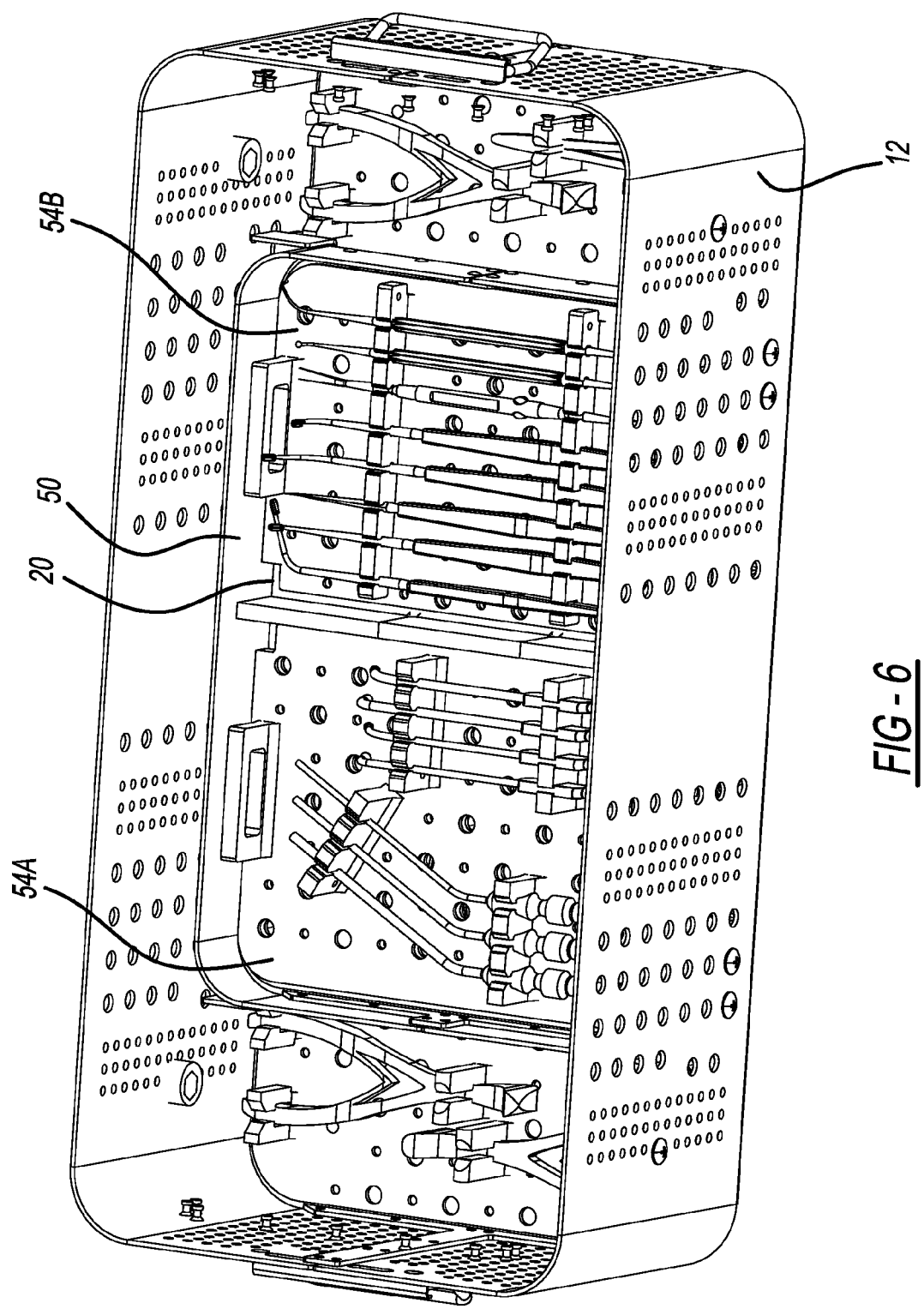
FIG. 6 is another perspective view of the container with a first instrument tray seated therein.
Figure 7:
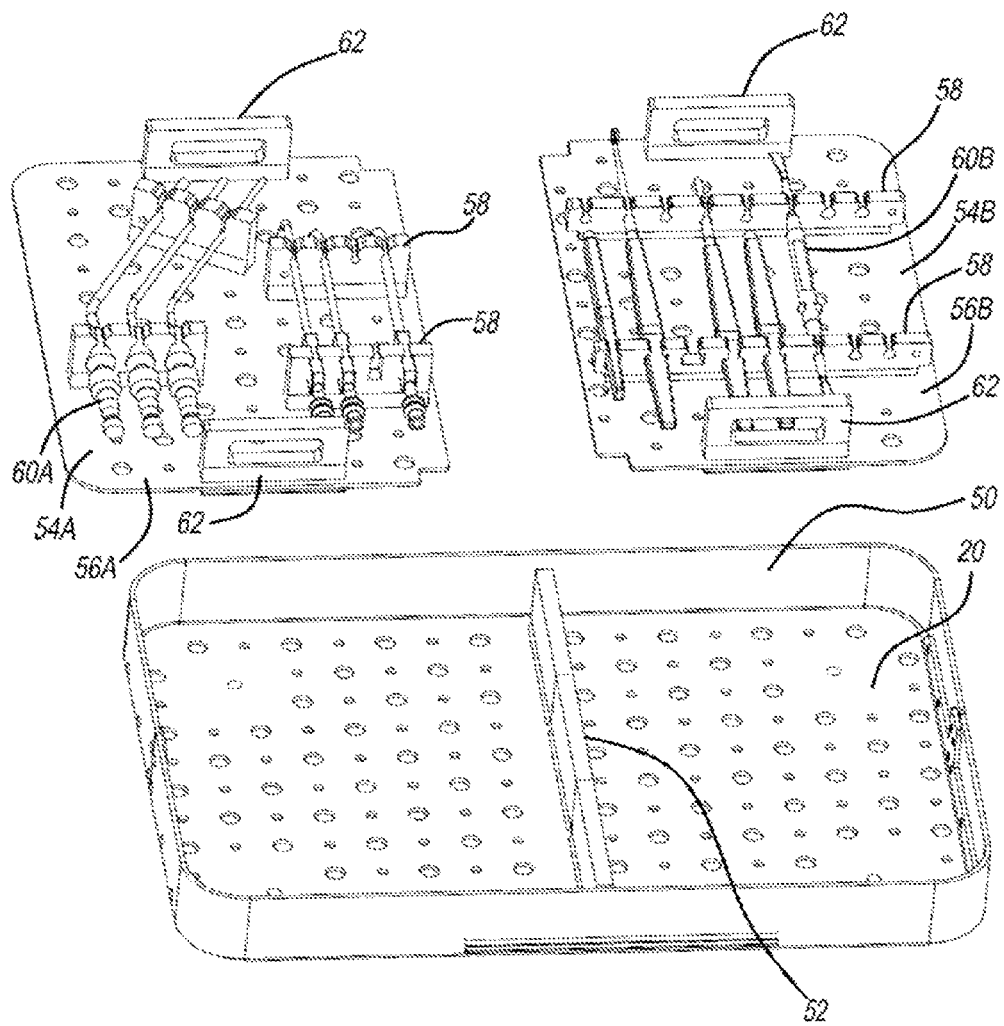
FIG. 7 illustrates the first instrument tray of FIG. 6 with a pair of tray inserts separated therefrom.

With additional reference to FIG. 6, the first tray 20 is illustrated seated within the storage chamber 28 on each of the first, second, third, and fourth retention flanges 40A-40D. With continued reference to FIG. 6 and additional reference to FIG. 7, the first tray 20 generally includes a first tray sidewall 50 extending about a perimeter of the first tray 20.

Extending across the first tray 20 to generally divide the first tray 20 in half, is a first tray divider 52. The first tray divider 52 can be any suitable feature or device to divide a first tray 20 generally in half, such as a nylon divider wall. The first tray divider 52 can be secured to the first tray 20 in any suitable manner, such as with a suitable adhesive or a suitable mechanical connection.

The first tray 20 includes a pair of first tray inserts 54A and 54B. Each of the first tray inserts 54A and 54B include a base 56A and 56B respectively with suitable instrument retention members 58 extending therefrom. The instrument retention members 58 can be any suitable devices or features to retain surgical instruments thereto, such as ENT instruments. For example, the members 58 can be made of a flexible and resilient autoclavable nylon material configured to cooperate with or clamp onto the surgical instruments to retain the surgical instruments to the first and second tray inserts 54A and 54B. Each base 56A and 56B can include instrument outlines 60A and 60B respectively to facilitate positioning of the instruments on the bases 56A and 56B. Any other suitable designation or identifier representing one or more particular surgical instruments may also be included on the bases 56A and 56B to further facilitate placement of the instruments, such as the designations "L," "M," "S," which designate large, medium, and small respectively. The first tray inserts 54A and 54B can further include handles 62 extending from the bases 56A and 56B respectively to facilitate removal of the first tray inserts 54A and 54B from the first tray 20.

Figure 8:
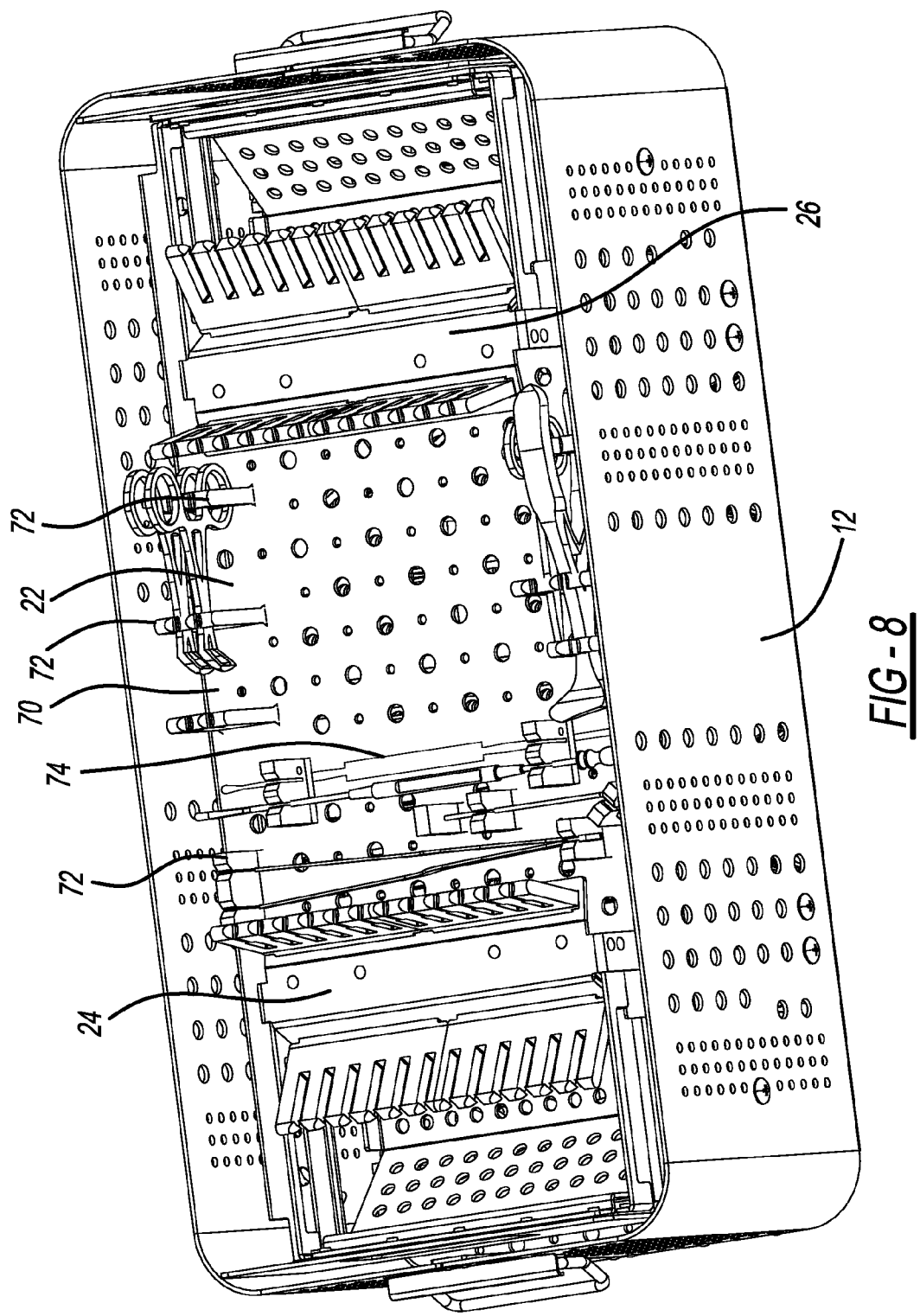
FIG. 8 is a perspective view of the container with a second instrument tray seated over and covering the first instrument tray.
Figure 9:
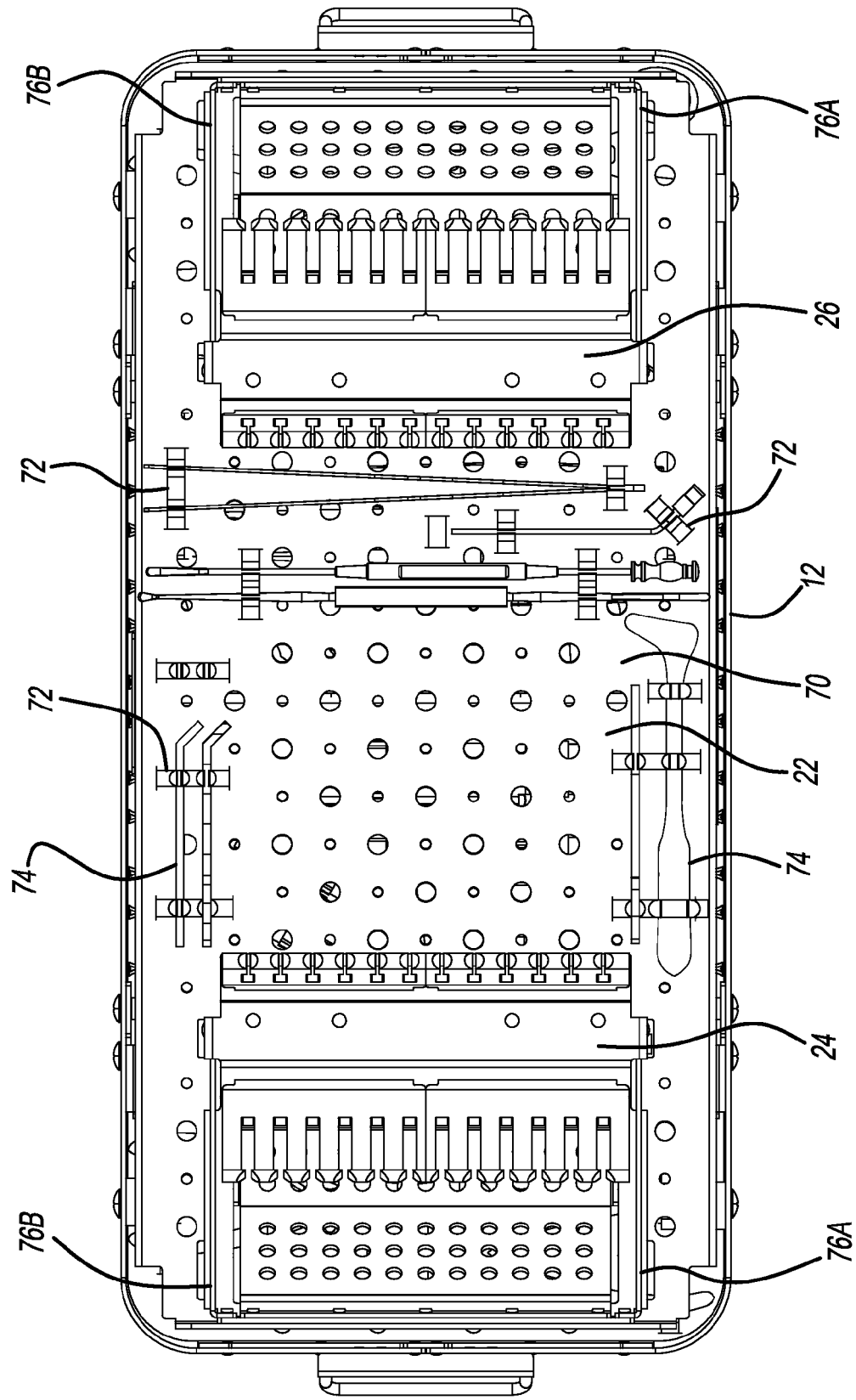
FIG. 9 is a top view of the second instrument tray seated in the container.

With additional reference to FIG. 8, the second tray 22 is illustrated seated within the storage chamber 28 above the first tray 20 and spaced apart from the first tray 20. Specifically, the second tray 22 is seated on each of the first, second, third, and fourth retention pins 46A-46D to suspend the second tray 22 above the first tray 20. With continued reference to FIG. 8 and additional reference to FIGS. 9-11, the second tray 22 includes a base 70, which is generally planar and sized to extend from the first sidewall 14A to the second sidewall 14B of the container 12. Extending generally vertically from the base 70 are a plurality of instrument retention features 72 arranged and configured to retain any suitable surgical instrument, such as ENT surgical instruments, to the second tray 22. Instrument outlines 74 can also be included on the base 70 to facilitate placement of the surgical instruments thereon.

Figure 10:
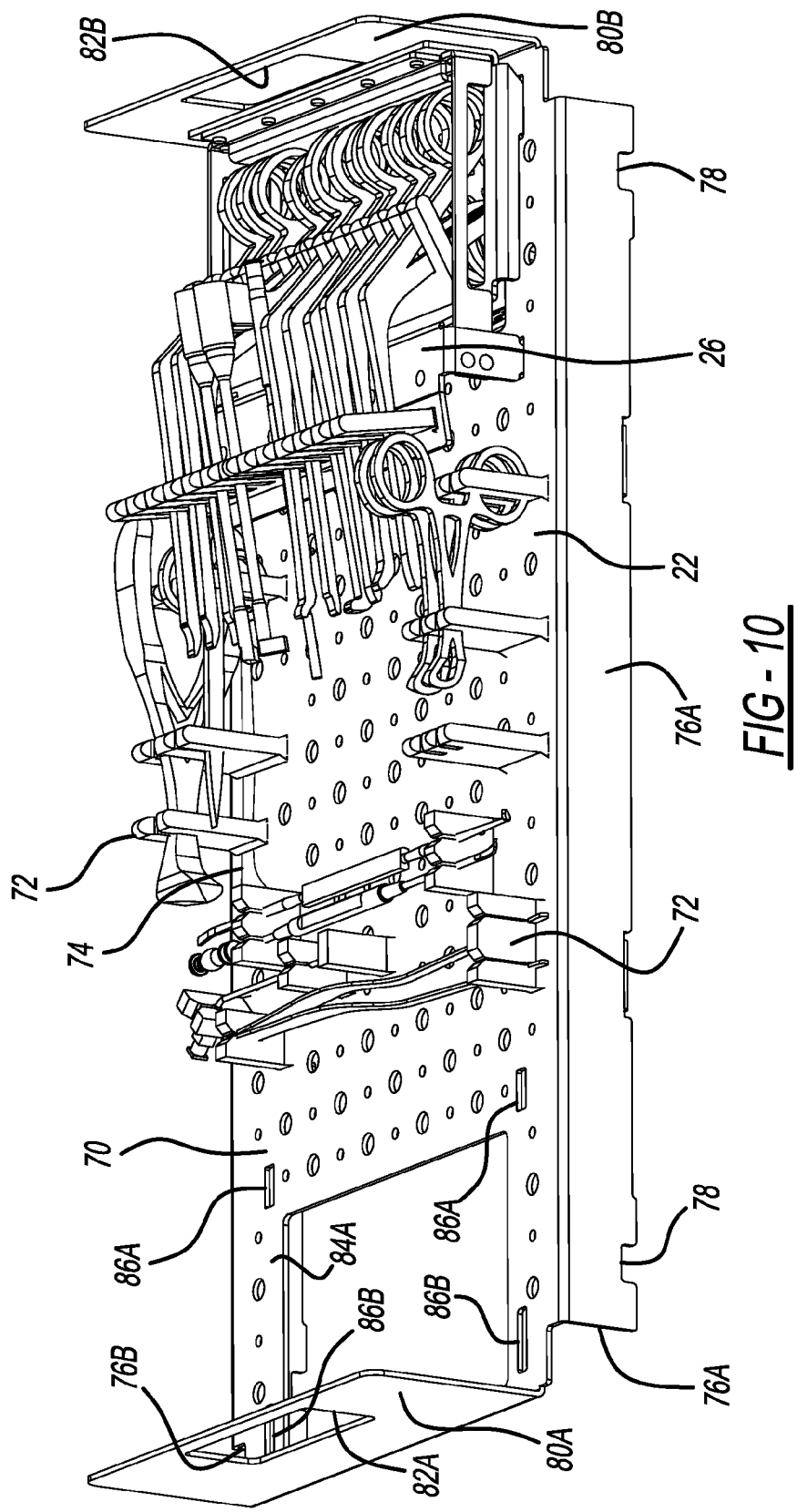
FIG. 10 illustrates the second instrument tray separated from the container.
Figure 11:
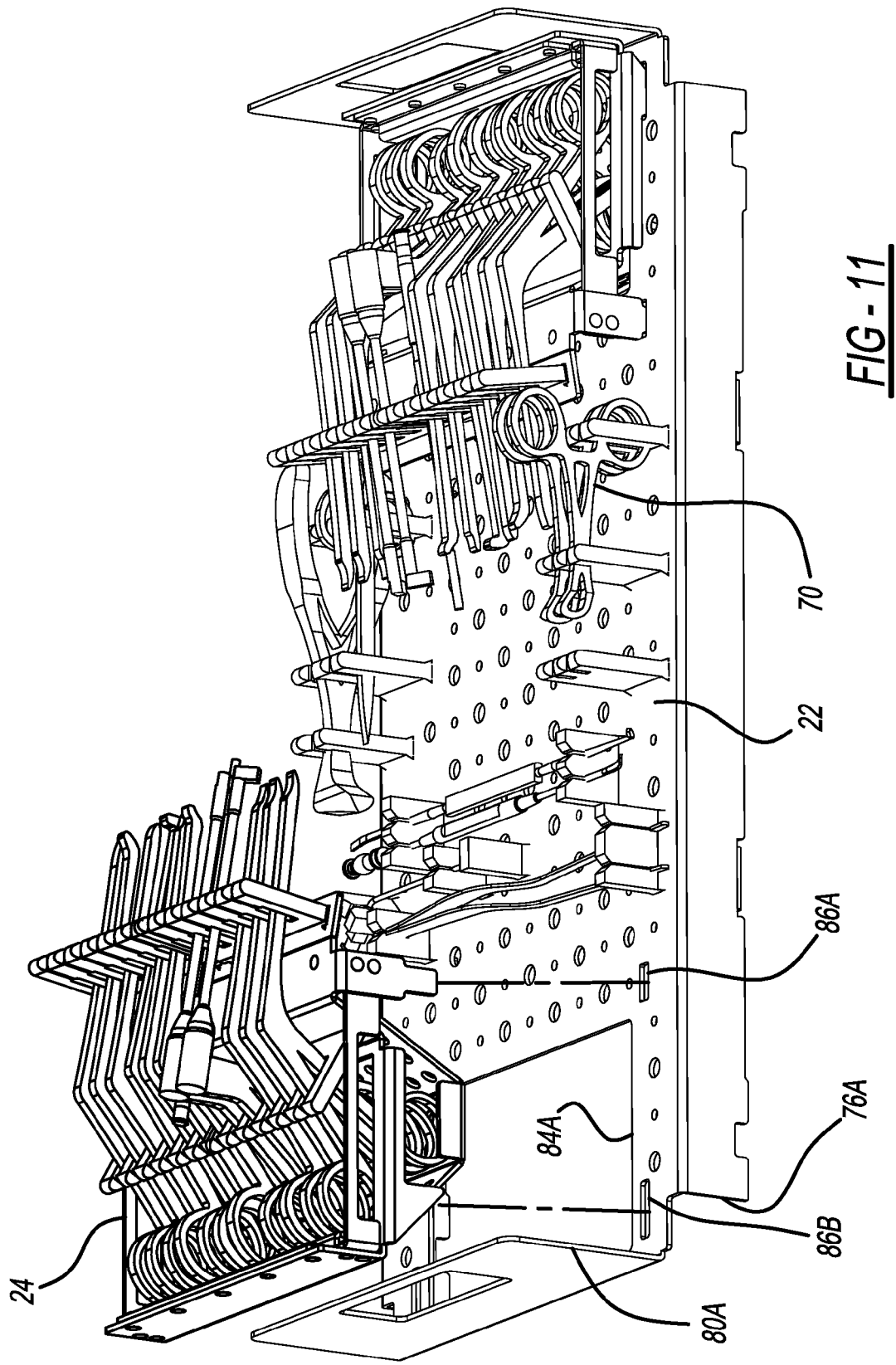
FIG. 11 illustrates a first rack being removed from cooperation with the second instrument tray.

As illustrated in FIG. 10 for example, the second tray 22 further includes a first flange 76A extending downward from the base 70 generally along the length of the tray 22. A second flange 76B extends downward from the base 70 from a side of the second tray 22 generally opposite to the first flange 76A, which can be seen in FIGS. 2, 4, 9, and 10, for example. Each of the first flange 76A and the second flange 76B define recesses 78 at opposite ends thereof. The recesses 78 are generally sized and arranged to individually cooperate with a different one of a first, second, third, and fourth retention pins 46A-46D to support the second tray 22 within the storage chamber 28 above the first tray 20.

The second tray 22 further includes first and second handles 80A and 80B respectively at opposite ends of the second tray 22 to facilitate insertion and withdrawal of the second tray 22 within the storage chamber 28. The first handle 80A defines a first opening 82A and the second handle 80B defines a second opening 82B to facilitate grasping of the first handle 80A and the second handle 80B respectively.

The base 70 defines a first aperture 84A proximate to the first handle 80A and a second aperture 84B proximate to the second handle 80B. As further described herein, the first aperture 84A is configured to receive the first instrument rack 24 and the second aperture 84B is configured to receive the second instrument rack 26. Proximate to the first aperture 84A and the second aperture 84B, the base 70 defines a plurality of receptacles 86A for receiving portions of the first and second instrument racks 24 and 26 to retain the instrument racks 24 and 26 substantially planar to the base 70. Proximate to each of the first handle 80A and the second handle 80B, the base 70 defines receptacles 86B, which receive an additional portion of the first and second racks 24 and 26 to further retain the first and second racks 24 and 26 to the second tray 22 as further described herein.

Figure 12:
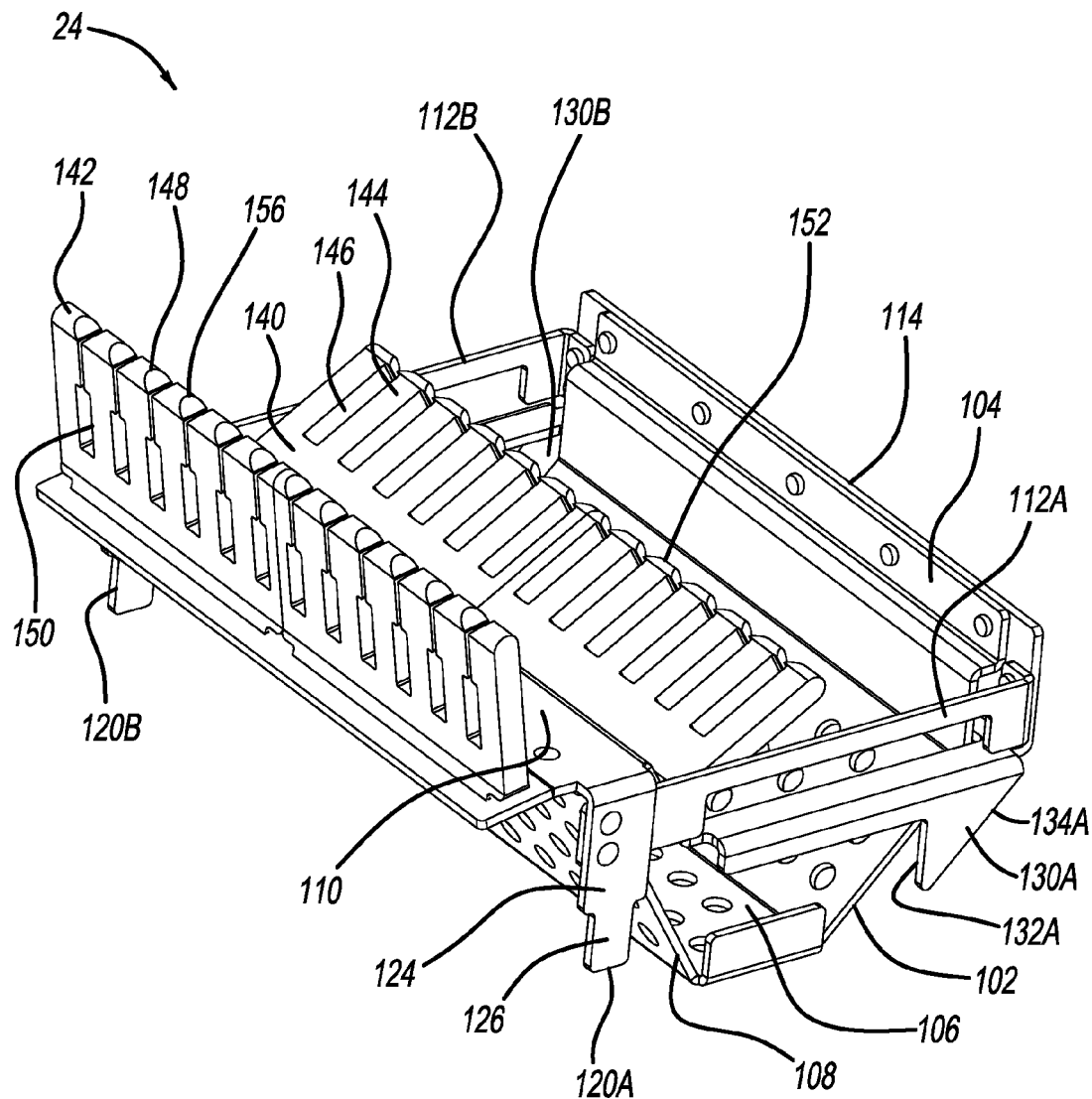
FIG. 12 is a perspective view of the first rack of the modular instrument kit.

With additional reference to FIGS. 12 and 13, the first instrument rack 24 will be described in detail. The first instrument rack 24 includes a rack base 102, which is generally planar. Extending from a first side of the rack base 102 is a base flange 104. The base flange 104 extends from the rack base 102 generally at an angle. Extending from a second side of the rack base 102 that is opposite to the first side, is an intermediate rack portion 106, which also extends from the rack base 102 at an angle. Extending from a side of the intermediate rack portion 106 opposite of the rack base 102 is a rack rear wall 108. The rack rear wall 108 extends from the intermediate rack portion 106 at an angle such that both the rack rear wall 108 and the rack base 102 generally oppose one another.

The first instrument rack 24 further includes an instrument support base 110. The instrument support base 110 is proximate to, or extends from, the rack rear wall 108. The instrument support base 110 is further supported by a first post 112A and a second post 112B, which are arranged on opposite sides of the base flange 104 and connected to a flange support 114 to which the base flange 104 is mounted to. The instrument support base 110 extends between the first post 112A and the second post 112B.

Extending from a first side of the instrument support base 110 is a first rack flange 120A, which extends over the first post 112A. Similarly, the second rack flange 120B extends from a side of the instrument support base 110 that is opposite to the first rack flange 120A. The second rack flange 120B extends over the second post 112B. Each of the first rack flange 120A and the second rack flange 120B include a proximal portion 124 and a distal portion 126. The proximal portion 124 is between the instrument support base 110 and the distal portion 126. The proximal portion 124 is mounted directly to either the first post 112A or the second post 112B and is generally wider than the distal portion 126.

Mounted to the first post 112A is a first coupling member 130A, and mounted to the second post 112B is a second coupling member 130B. Each of the first and second coupling members 130A and 130B include a first portion 132A and 132B (see FIGS. 17 and 18 for example) respectively that extends generally parallel to the distal portions 126 of the first and second rack flanges 120A. Extending from each of the first portion 132A and 132B are second portions 134A and 134B respectively. The second portions 134A and 134B extend generally co-planar with the rack base 102, and thus further support the first instrument rack 24 in an upright position when seated on a flat surface at a first location. The first and second coupling members 130A and 130B are generally sized and shaped to be received within the receptacles 86B of the second tray 22, and the first and second rack flanges 120A and 120B are sized and shaped to be received within the receptacles 86A of the second tray 22 to couple the first instrument rack 24 to the second tray 22 at the first aperture 84A such that the rack base 102, the intermediate rack portion 106, and at least the rack rear wall 108 extend through the first aperture 84A, with the remainder of the first instrument rack 24 being supported on the base 70 of the second tray 22.

The first instrument rack 24 further includes a first instrument support 140 and a second instrument support 142. The first instrument support 140 extends from the instrument support base 110 generally towards the base flange 104. The second instrument support 142 extends from the instrument support base 110 in a direction generally opposite to the direction in which the first and second rack flanges 120A and 120B extend. The first and second instrument supports 140 and 142 extend from the instrument support base 110 at generally opposite ends of the instrument support base 110. The first instrument support 140 includes a plurality of teeth 144 that are spaced apart to define slots 146 therebetween. Similarly, the second instrument support 142 includes a plurality of teeth 148, which define a plurality of slots 150 therebetween. The teeth 144 of the first instrument support 140 are somewhat narrower than the teeth 148 of the second instrument support 142, and thus the slots 146 are generally wider than the slots 150. Furthermore, the teeth 144 include a tip portion 152 and the teeth 148 include a tip portion 146, which are each generally wider than the remainder of the teeth 144 and 148 respectively associated therewith. The tips 152 and 156 are operable to facilitate retention of instruments in the slots 146 and 150.

The first instrument support 140 and the second instrument support 142 can be made of any suitable autoclavable material that is generally flexible and resilient to retain instruments between the teeth 144 and 148 respectively. For example, the first instrument support 140 and the second instrument support 142 can be made of a suitable flexible silicone. The first instrument support 140 and the second instrument support 142 can each be secured to the instrument support base 110 in any suitable manner, such as with a suitable adhesive or mechanical connection. The second instrument rack 26 is substantially similar, and may be identical to, the first instrument rack 24, and thus the description of the first instrument rack 24 is also sufficient to describe the second instrument rack 26.

Figure 13:
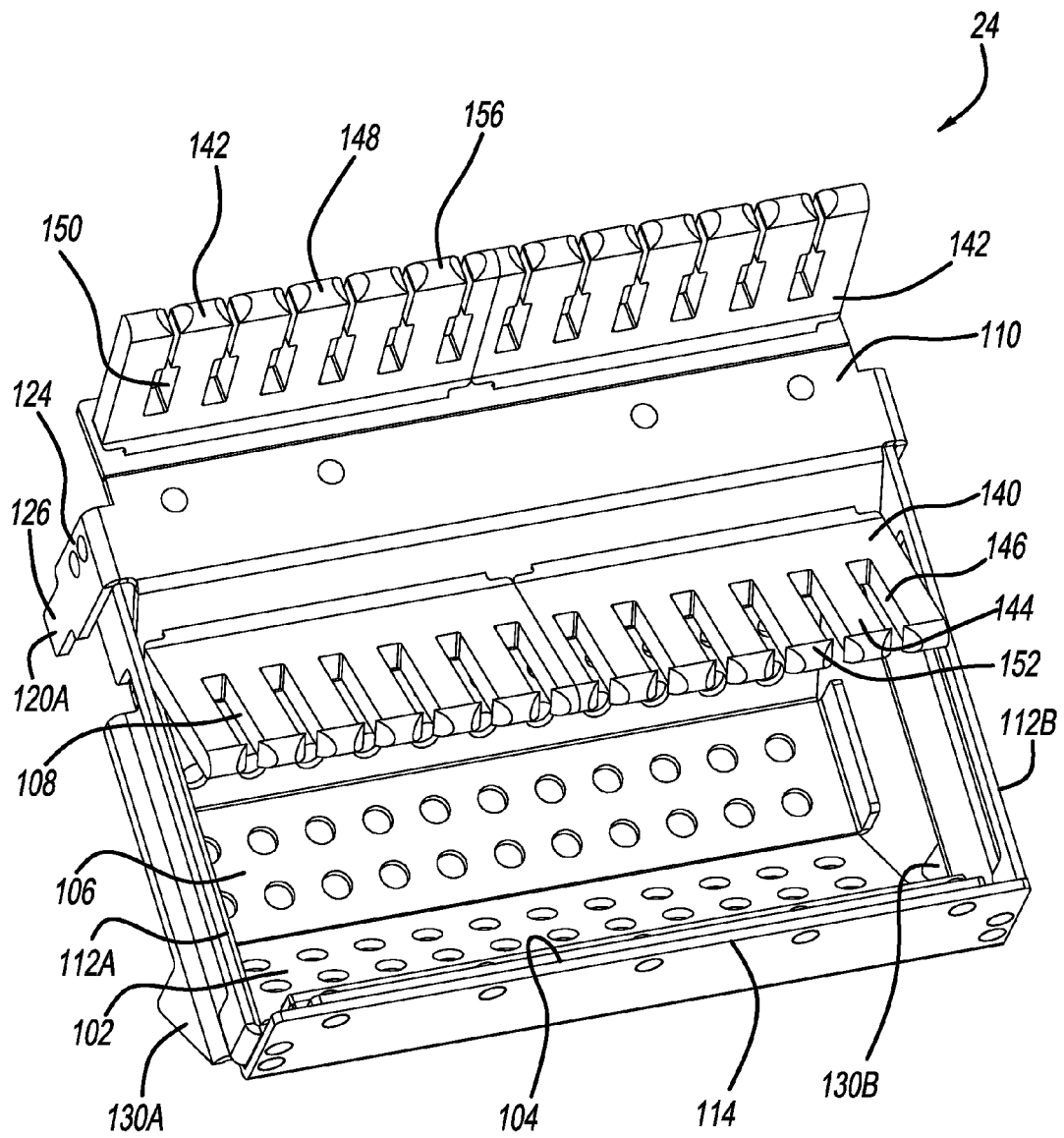
FIG. 13 illustrates the first rack separated from the modular instrument kit and seated upright on a flat surface.
Figure 14:
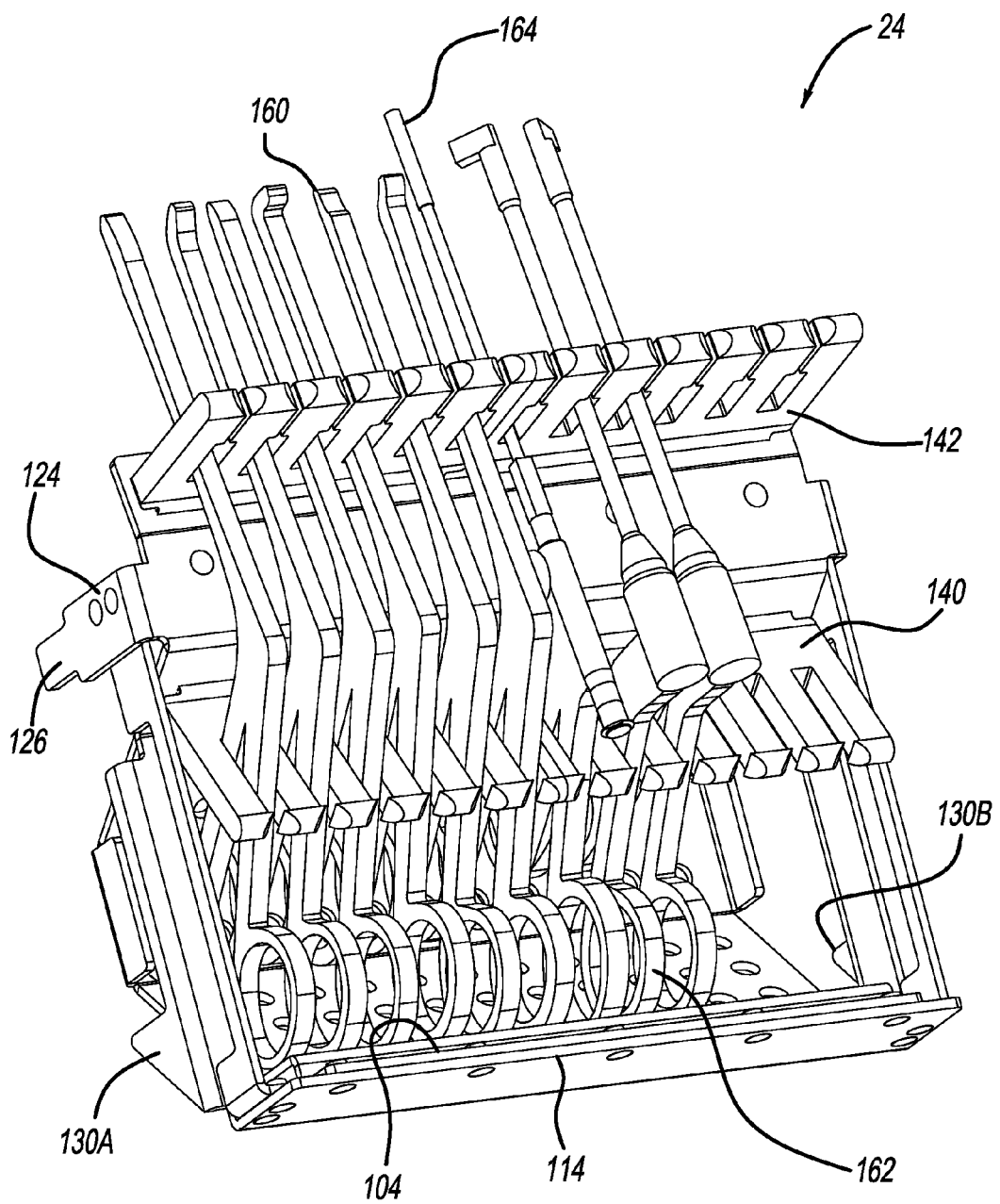
FIG. 14 is similar to FIG. 13 and includes a plurality of surgical instruments mounted to the first rack.
Figure 15:
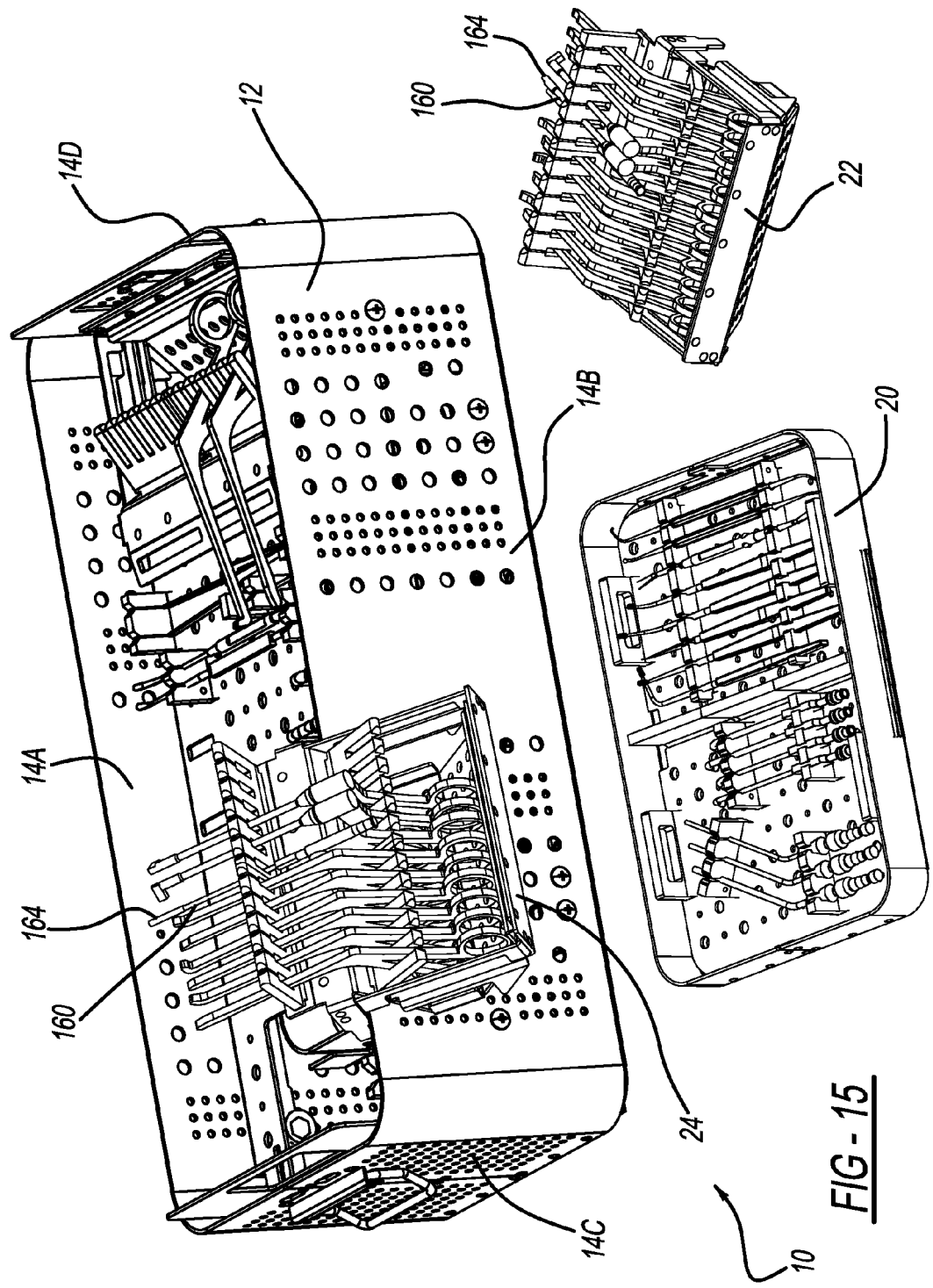
FIG. 15 illustrates the first rack coupled to a sidewall of the container, as well as the first tray and a second rack seated spaced apart from the container.
Figure 16:
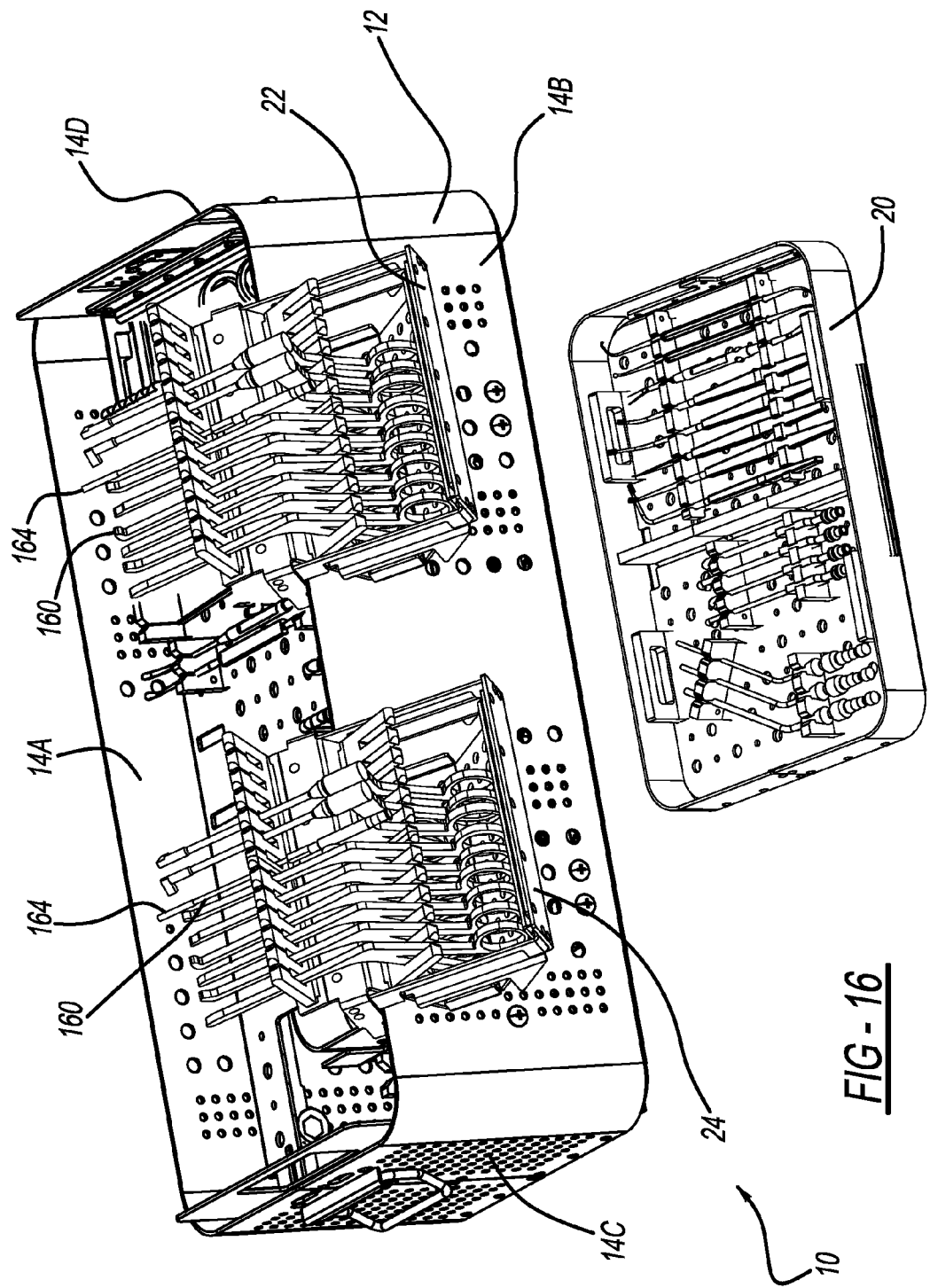
FIG. 16 is similar to FIG. 15, but with both the first rack and the second rack mounted to the sidewall of the container.

With reference to FIGS. 13 and 14 for example, the first instrument rack 24 can be self-supported in an upright position when the rack base 102 is seated on a planar surface at a first location. As illustrated in FIG. 14, when seated on a planar surface, the first instrument rack 24 will support instruments in a generally upright position, such as forceps 160. As illustrated in FIGS. 14-16, the forceps 160 are arranged such that a handle 162 of each of the forceps 160 is seated against, or proximate to, base flange 104. The tips 164 are thus arranged such that they extend generally upright from the second instrument support 142. Portions of the forceps 160 between the handles 162 and the tips 164 are arranged within the slots 146 and 150 of the first and second instrument supports 140 and 142 respectively to retain the forceps 160 in cooperation with the first instrument rack 24. Although the instruments are illustrated as forceps 160, any suitable instrument, particularly an ENT instrument, can be coupled to the first instrument rack 24. Furthermore, the orientation of the instruments can be generally reversed such that the handles 162 are upright and extend generally vertically, and the tips 164 are seated against, or proximate to, base flange 104.

Supporting the tips 164 upright as illustrated in FIG. 14 is advantageous for a number of reasons. For example, the surgeon or other operating room personnel can easily view the tips 164 and thus distinguish between different types of, for example, forceps 160. Because the handles 162 of the different forceps 160 are identical or similar, it would be difficult to distinguish between the different forceps 160 if the tips 164 were not clearly visible. The visibility of the tips 164 is enhanced when in the upright position of FIG. 14 because the unidirectional lights typically used in an operating room will clearly illuminate the tips 164, and by arranging the tips 164 upright apart from other structural features of the first instrument rack 24, shadows caused by the unidirectional operating room lights will be diminished, and thus the vision of the surgeon or other operating room personnel will not be obstructed and he or she will be able to easily select the desired forceps 160. To further facilitate selection of the desired forceps 160, the instrument support base 110 includes a plurality of visual indicators, such as the numerals "1" through "12" aligned with each of the slots 146 and 150. Therefore, if a particular surgical procedure calls for an instrument arranged in slots 146 and 150 designated with number "1," the surgeon or appropriate operating room personnel will be able to clearly identify position number "1" and select the forceps 160 seated at that position.

With additional reference to FIGS. 15-21, the first instrument rack 24 and/or the second instrument rack 26 can be coupled to any of the sidewalls 14A-14D of the container 12 at a second location, particularly the longer sidewalls 14A and 14B. Coupling the first and/or second instrument racks 24 and 26 to the container 12 is advantageous for a plurality of different reasons. For example, suspending the first and/or second instrument racks 24 and 26 on the container 12 will free valuable operating room space and suspend the instruments, such as the forceps 160, above other surgical instruments, thereby making it easier to select the desired forceps 160 and eliminate shadows that may be caused by the unidirectional operating room lights when the lights contact surrounding instrumentation and/or equipment. The first and/or second instrument racks 24 and 26 can be coupled to any vertical or generally vertical surface in the same way that the racks 24 and 26 are coupled to the sidewalls 14A-14D of the container 12. For example, the first and/or second instrument racks 24 and 26 can be coupled to an operating room table. Therefore, the first and/or the second instrument racks 24 and 26 can be generally integral with the operating room and other devices of the operating room to facilitate accesses to and use of instruments seated on or in the instrument racks 24 and 26, and thus increase the efficiency and overall ease of the surgical procedure.

The first and second instrument racks 24 arrange the forceps 160 at generally a 45 degree angle, which further facilitates viewing of the tips 164 and the ability to distinguish between the tips 164. Coupling the first and second instrument racks 24 and 26 to the container sidewalls 14A and 14B further protects the forceps 160 from being damaged by positioning the tips 164 spaced apart from surrounding equipment, which could damage the tips 164 should the equipment accidentally come into contact with the tips 164.

Figure 17:
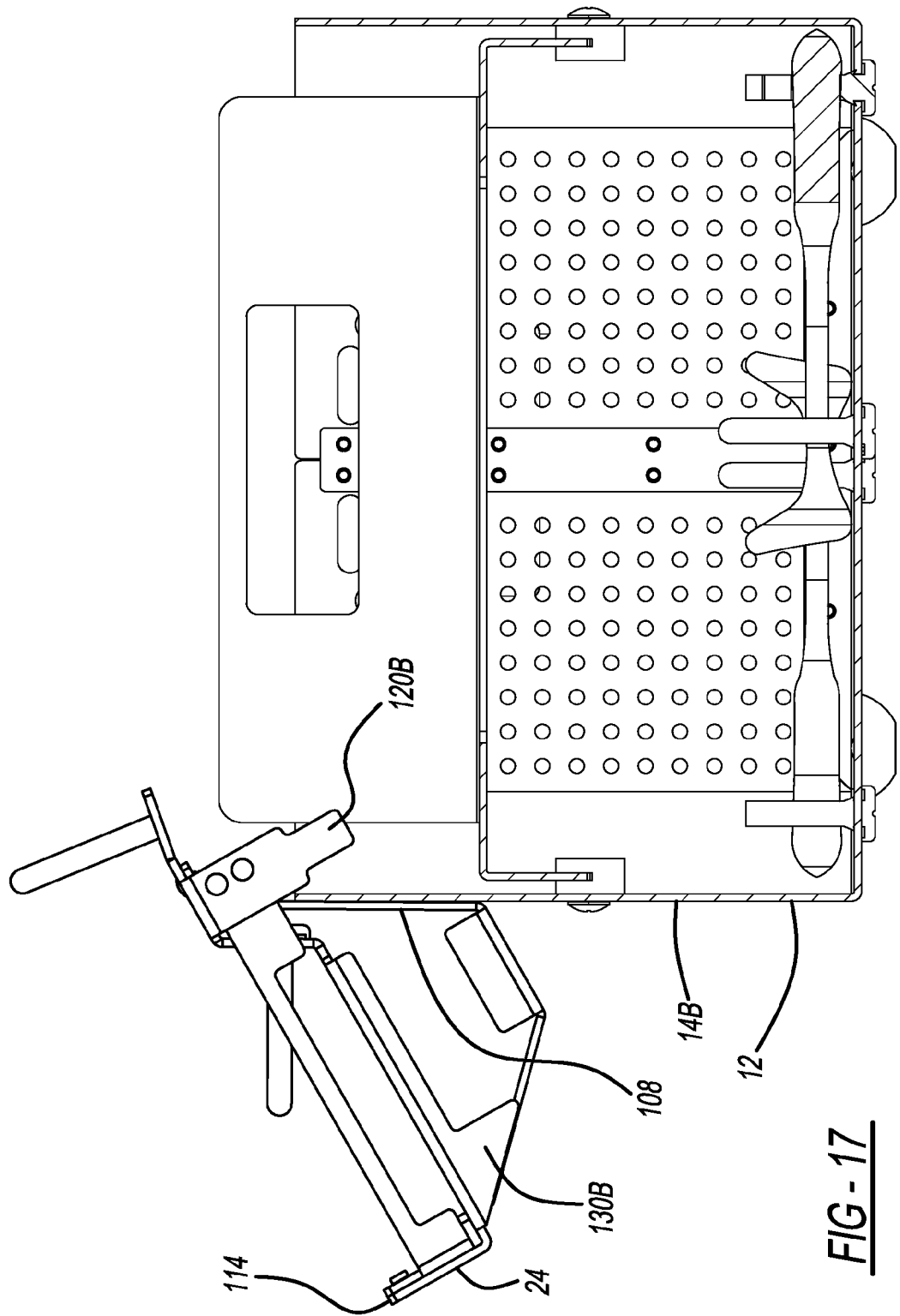
FIG. 17 is a side view of the first rack coupled to the sidewall of the container.
Figure 18:
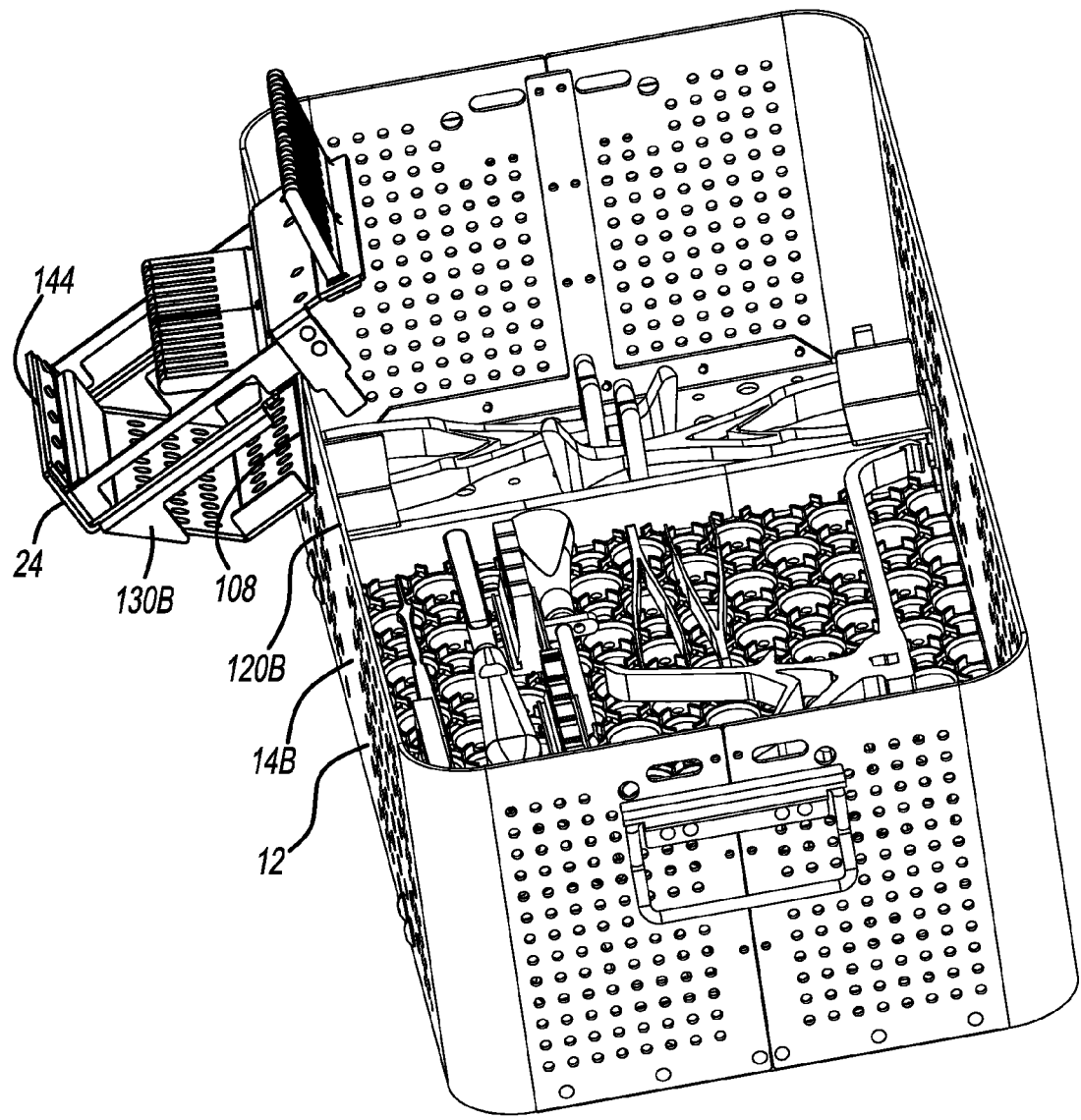
FIG. 18 is another view of the first rack coupled to the sidewall of the container.
Figure 19:
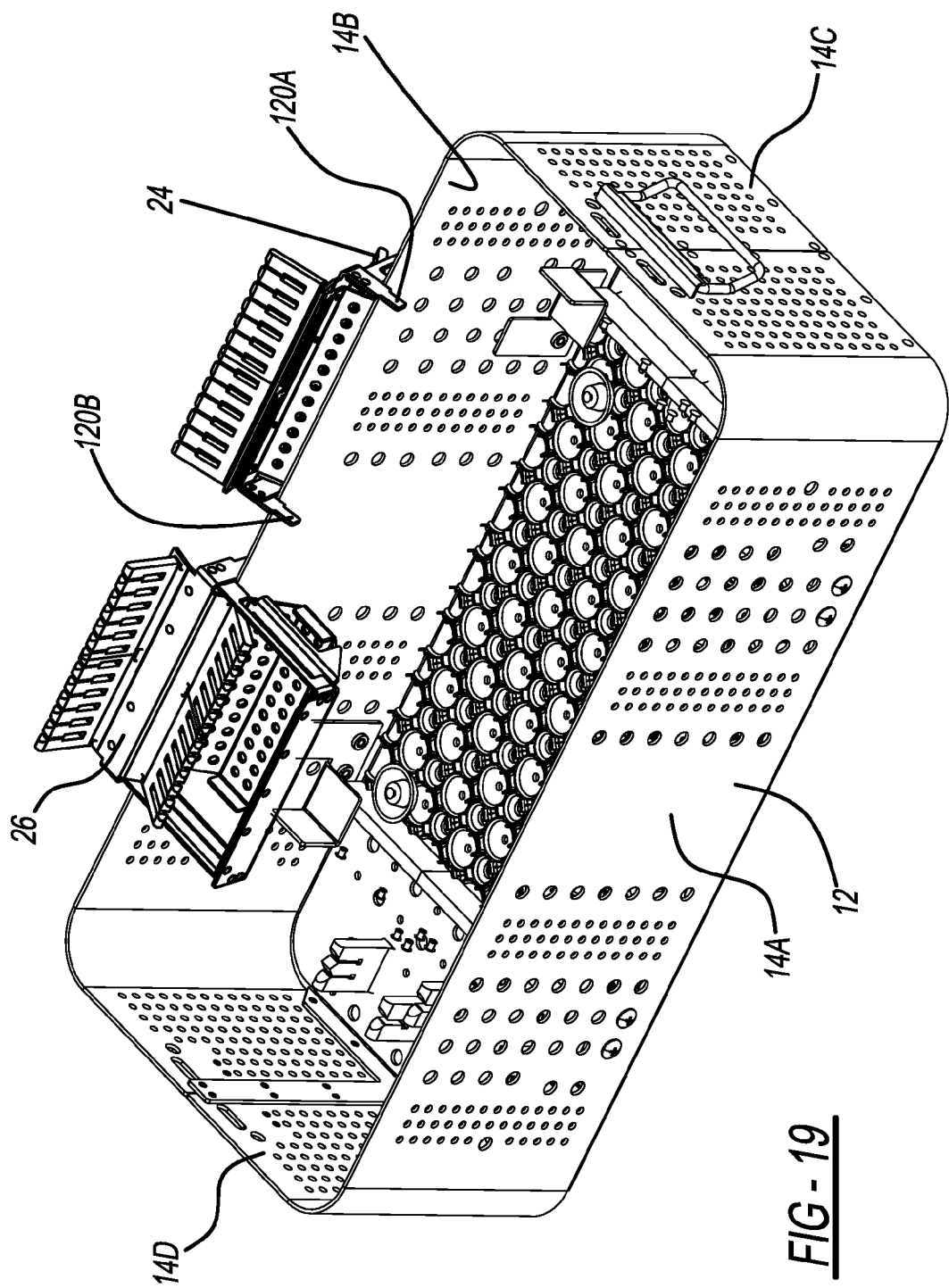
FIG. 19 illustrates both the first rack and the second rack coupled to the sidewall of the container on opposite sides of the sidewall.
Figure 20:
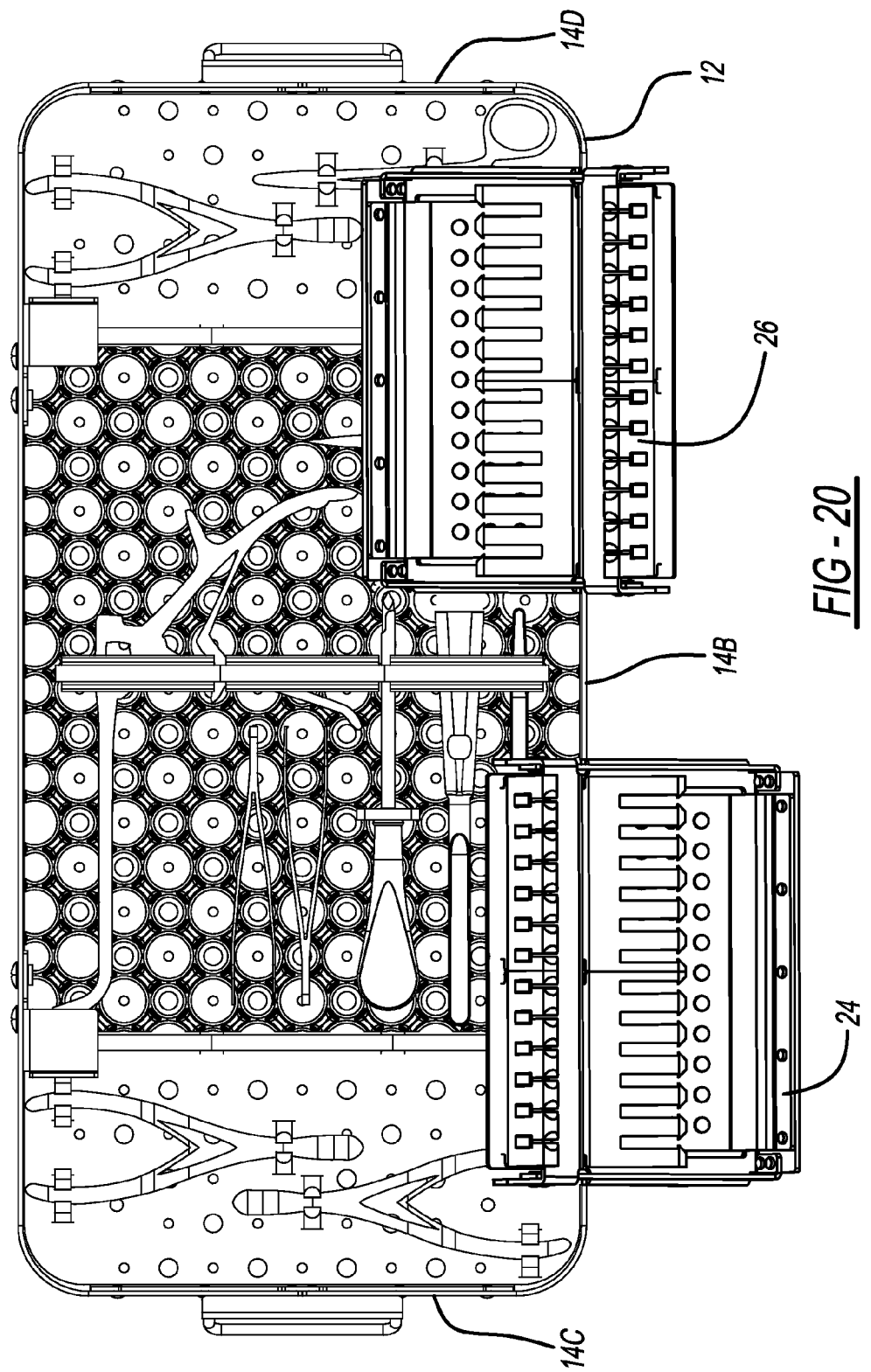
FIG. 20 is a top view of the first and second racks coupled to opposite sides of the sidewall of the container.
Figure 21:
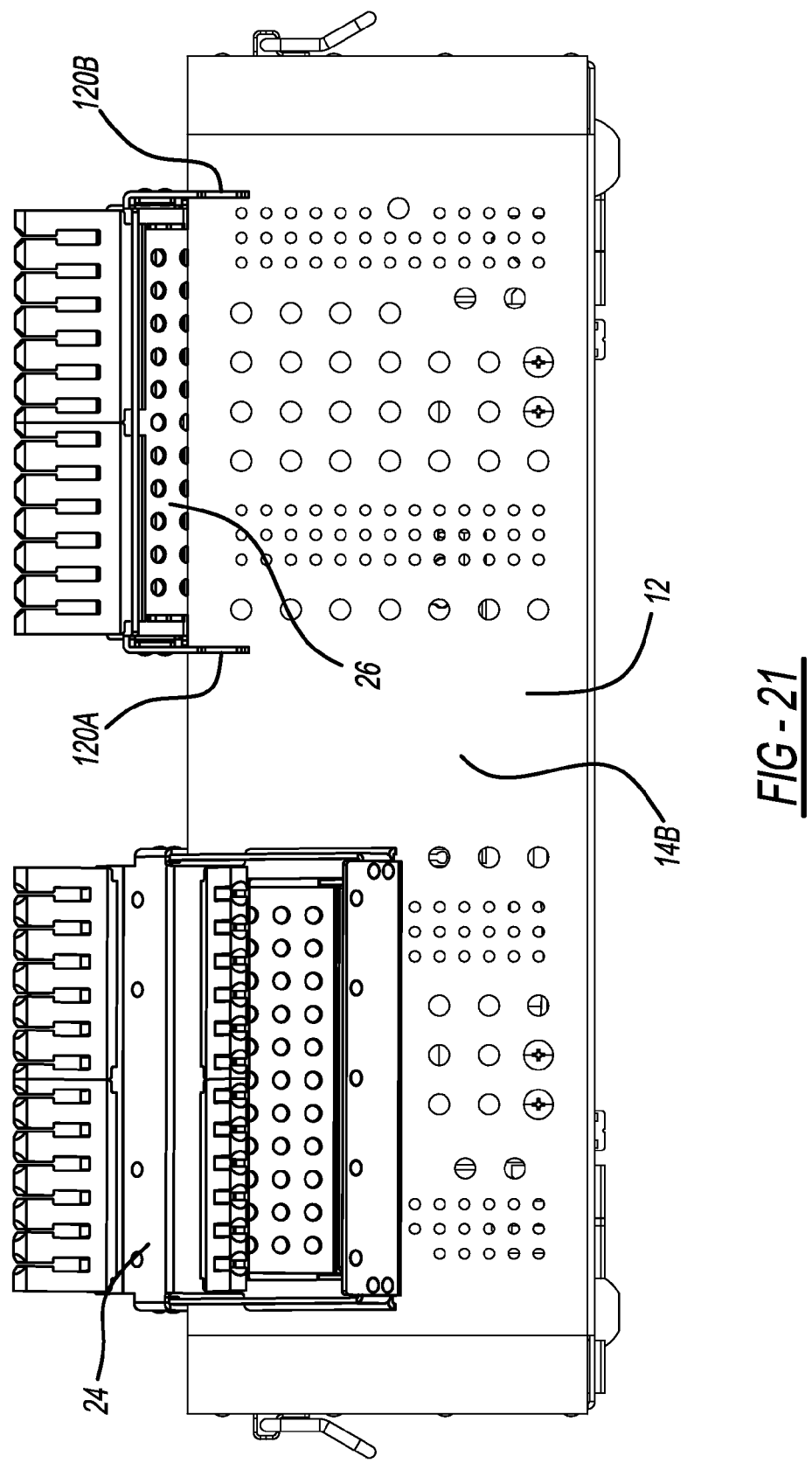
FIG. 21 is a general side view of the container illustrating the first and second racks mounted to the sidewall on opposite sides of the sidewall.

As illustrated in FIGS. 17 and 18, for example, the first and second instrument racks 24 are arranged such that the rack rear wall 108 contacts the desired sidewall 14A-14D and is generally flush with the particular sidewall 14A-14D. The first and second rack flanges 120A and 120B extend over the particular sidewall 14A-14D such that the distal portion 126 contacts a surface of the sidewall 14A-14D that is opposite to the surface that the rack rear wall 108 abuts. Therefore, the particular sidewall 14A-14D is arranged and wedged between the rack rear wall 108 and the first and second rack flanges 120A and 120B. The first and second rack flanges 120A and 120B together with the rack rear wall 108 and the rack base 102 generally provide a coupling mechanism. As illustrated in FIG. 19, the first and second instrument racks 24 and 26 can be coupled to opposite sides of any of the sidewalls 14A-14D.

The modular instrument kit 10 can be configured to present instruments to the surgeon or other suitable operating room personnel in the anticipated order of use during a particular surgical procedure. For example, instruments that are likely to be used early in the surgical procedure, such as the forceps 160, can be arranged proximate to the lid 16 such that upon removal of the lid 16 the instruments may be accessed first. Instruments that are likely to be used later during the surgical procedure, or instruments that may be optional or less likely to be used at all, may be arranged deep within the container 12, such as on the instrument storage pad 32. Instrumentation that is likely to be used during the midpoint of the surgical procedure may be arranged on either the second tray 22 or the first tray 20 with instrumentation to be used earlier during the procedure mounted to the second tray 22, while instrumentation likely to be used later during the procedure can be mounted to the first tray 20.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A modular instrument kit comprising:
a container;
a first tray comprising a first aperture; and
a first rack comprising
   a flange, wherein the first rack hangs via the flange from and over an upper edge of a sidewall of the container, and
   a first instrument support member that (i) supports a plurality of surgical instruments, and (ii) couples the plurality of surgical instruments to the first tray,
wherein
   the container receives the first tray and the first rack,
   the first tray receives and engages with the first rack,
   the first aperture receives the flange of the first rack when the first rack is being seated on the first tray, and
   insertion of the flange into the first aperture maintains placement of the first rack relative to the first tray.

2. The modular instrument kit of claim 1, wherein:
the first rack comprises a plurality of instrument support members;
the plurality of instrument support members include the first instrument support member; and
the plurality of instrument support members such that tips of the plurality of surgical instruments extend upward to be readily viewable.

3. The modular instrument kit of claim 1, wherein the flange hangs the first rack from the sidewall with a wall of the first rack being flush against the sidewall.

4. The modular instrument kit of claim 3, wherein the flange contacts the upper edge of the sidewall when the first rack is hanging from the sidewall.

5. The modular instrument kit of claim 1, wherein:
the first tray comprises a second aperture;
the first rack comprises a coupling member; and
the coupling member is received within the second aperture when the first rack is being seated on the first tray.

6. The modular instrument kit of claim 5, wherein:
the first tray comprises a base;
the rack comprises
   a support base,
   a rack wall that extends from the support base, and
   an intermediate member that extends from the rack wall; and
the first tray defines a receptacle that receives the rack wall and the intermediate member; and
the intermediate member is on an opposite side of the base of the first tray than the support base of the rack when the rack is seated on the first tray.

7. The modular instrument kit of claim 1, further comprising a second tray, wherein:
the second tray is received within the container; and
the first tray is received on the second tray.

8. The modular instrument kit of claim 1, further comprising a second rack that is received by and engages with the first tray.

9. The modular instrument kit of claim 1, further comprising a second rack that hangs via a second flange from the sidewall of the container.

10. The modular instrument kit of claim 1, further comprising:
a second rack that engages with the first tray when the second rack is seated on the first tray; and
a second tray received beneath the first tray and between portions of the first rack and the second rack.

11. A modular instrument kit comprising:
a container;
a first tray;
a first rack comprising
   a planar base,
   a wall connected to and extending from the base,
   a flange, and
   an instrument support member supports a plurality of surgical instruments; and
a second rack,
wherein
   the first rack hangs over and from an upper edge of a sidewall of the first tray with (i) the wall of the first rack flush against the sidewall, and (ii) the flange being in contact with the sidewall,
   the first rack supports the plurality of surgical instruments in an upright orientation when the first rack is hanging from the sidewall,
   the flange is received within a first aperture of the first tray when the first rack and the first tray are being seated within the container, and
   the second rack hangs from an opposite side of the sidewall than the first rack.

12. The modular instrument kit of claim 11, wherein the flange contacts the upper edge of the sidewall when the first rack is hanging from the sidewall.

13. The modular instrument kit of claim 11, wherein the flange extends over the upper edge of the sidewall when the first rack is hanging from the sidewall.

14. The modular instrument kit of claim 11, wherein a coupling member of the first rack is received within another aperture of the first tray when the first rack and the first tray are being seated within the container.

15. The modular instrument kit of claim 11, wherein:
the first tray defines a receptacle that receives at least a portion of the planar base of the first rack; and the planar base is on an opposite side of the first tray than the instrument support member.

16. The modular instrument kit of claim 11, wherein:
the flange is a first flange at a first end of the first rack;
the first rack includes a second flange;
the second flange is at a second end of the first rack; and
the first flange and the second flange engage with the first tray when the first rack is seated on the first tray.

17. The modular instrument kit of claim 11, wherein:
a first portion of the first rack extends through a second aperture of the first tray when the first rack is seated on the first tray; and
a second portion of the second rack extends through a third aperture of the first tray when the second rack is seated on the first tray.

18. A modular instrument kit comprising:
a container;
a first tray received within the container, the first tray including a plurality of instrument mounts and a first slot; and
a first rack comprising
a support base,
a planar base separate from the support base, wherein the planar base supports the first rack in an upright orientation on a planar surface,
an intermediate rack member connected between the support base and the planar base and received within an aperture of the first tray, wherein the intermediate rack member is on an opposite side of the first tray than the support base when the first rack is seated on the first tray,
a wall that extends from the support base through the aperture to the intermediate rack member when the first rack is seated on the first tray,
a flange extending from the first rack, wherein the first rack hangs via the flange from a sidewall of the container, wherein the flange engages with the first slot of the first tray when the first rack is seated on the first tray, and
an instrument support member that supports a plurality of surgical instruments and couples the plurality of surgical instruments to the first rack.

19. The modular instrument kit of claim 18, wherein the planar base is configured to support the first rack in an upright orientation on the planar surface such that the first rack supports the plurality of surgical instruments such that tips of the plurality of surgical instruments extend upward to be readily viewable.

20. The modular instrument kit of claim 18, wherein the first rack hangs from the sidewall via the flange with the wall of the first rack flush against the sidewall.

21. The modular instrument kit of claim 20, wherein the flange contacts an edge of the sidewall when the first rack is hanging from the sidewall.

22. The modular instrument kit of claim 18, wherein:
the first tray defines a second slot; and
the second slot receives a coupling member of the first rack.

23. The modular instrument kit of claim 18, further comprising:
a second rack that engages with the first tray and holds a second plurality of surgical instruments; and
a second tray comprising a plurality of inserts, wherein each of the plurality of inserts comprise a plurality of support members, and wherein the plurality of support members of the plurality of inserts support respectively a third plurality of instruments.

* * * * *